United States Patent
Mata et al.

(10) Patent No.: US 7,432,307 B2
(45) Date of Patent: *Oct. 7, 2008

(54) MODULATORS OF RETINOL-RETINOL BINDING PROTEIN (RBP)-TRANSTHYRETIN (TTR) COMPLEX FORMATION

(75) Inventors: Nathan L. Mata, La Jolla, CA (US); Kenneth Widder, Rancho Santa Fe, CA (US); Jay Lichter, San Diego, CA (US)

(73) Assignee: Sirion Therapeutics, Inc., Tampa, FL (US)

(*) Notice: Subject to any disclaimer, the term of this patent is extended or adjusted under 35 U.S.C. 154(b) by 307 days.

This patent is subject to a terminal disclaimer.

(21) Appl. No.: 11/267,395

(22) Filed: Nov. 4, 2005

(65) Prior Publication Data

US 2006/0094063 A1    May 4, 2006

Related U.S. Application Data

(60) Provisional application No. 60/672,405, filed on Apr. 18, 2005, provisional application No. 60/660,904, filed on Mar. 11, 2005, provisional application No. 60/629,695, filed on Nov. 19, 2004, provisional application No. 60/625,532, filed on Nov. 4, 2004.

(51) Int. Cl.
*A61K 31/07* (2006.01)

(52) U.S. Cl. .................. 514/725; 514/613; 514/699; 514/741; 514/912

(58) Field of Classification Search .................. 435/7.1, 435/7.93; 436/504, 544, 545, 546, 172; 568/425; 514/725, 613, 699, 741, 912
See application file for complete search history.

(56) References Cited

U.S. PATENT DOCUMENTS

| | | |
|---|---|---|
| 4,190,594 A | 2/1980 | Gander et al. |
| 4,323,581 A | 4/1982 | Gander |
| 4,665,098 A | 5/1987 | Gibbs et al. |
| 4,743,400 A | 5/1988 | Maryanoff |
| 4,874,795 A | 10/1989 | Yessair |
| 5,023,252 A | 6/1991 | Hseih |
| 5,314,909 A | 5/1994 | Dollerup |
| 5,399,757 A | 3/1995 | Maryanoff |
| 5,427,571 A | 6/1995 | Sells |
| 5,596,011 A * | 1/1997 | Repine et al. ............ 514/369 |
| 5,776,915 A | 7/1998 | Peterson et al. |
| 5,814,612 A | 9/1998 | Buck et al. |
| 6,034,211 A | 3/2000 | Kelly |
| 6,051,692 A | 4/2000 | Bandman et al. |
| 6,075,032 A | 6/2000 | Campochiaro et al. |
| 6,093,706 A | 7/2000 | Zeligs |
| 6,128,870 A | 10/2000 | Kohler |
| 6,458,029 B2 | 10/2002 | Morris |
| 6,482,802 B1 | 11/2002 | Hu et al. |
| 6,503,242 B1 | 1/2003 | Ellsberry |
| 6,506,917 B1 | 1/2003 | Evans et al. |
| 6,599,891 B2 * | 7/2003 | North et al. ............ 514/183 |
| 6,696,606 B2 | 2/2004 | Curley, Jr. et al. |
| 6,875,767 B2 | 4/2005 | Bilodeau et al. |
| 2002/0031539 A1 | 3/2002 | Plutzky et al. |
| 2002/0128291 A1 | 9/2002 | Campochiaro et al. |
| 2002/0143062 A1 | 10/2002 | Lopez-Berestein et al. |
| 2002/0183394 A1 | 12/2002 | Gupta et al. |
| 2002/0193065 A1 | 12/2002 | Morris et al. |
| 2003/0004418 A1 | 1/2003 | Marmorstein |
| 2003/0022831 A1 | 1/2003 | Rothbard et al. |
| 2003/0032078 A1 | 2/2003 | Travis |
| 2004/0092435 A1 | 5/2004 | Peyman |
| 2004/0102650 A1 | 5/2004 | Curley, Jr. et al. |
| 2004/0177387 A1 | 9/2004 | Jayakrishna |
| 2006/0069078 A1 * | 3/2006 | Rando .................. 514/183 |
| 2006/0135469 A1 | 6/2006 | Widder et al. |
| 2006/0167088 A1 | 7/2006 | Widder et al. |
| 2007/0015827 A1 | 1/2007 | Widder et al. |

FOREIGN PATENT DOCUMENTS

| | | |
|---|---|---|
| DE | 3610531 A1 | 10/1986 |
| DE | 10038641 A1 | 2/2002 |
| EP | 0258865 B1 | 11/1990 |
| JP | 11-503998 | 6/1999 |
| WO | WO-99-08682 A1 | 2/1999 |
| WO | WO00/21528 | 4/2000 |
| WO | WO-2001-19770 A2 | 3/2001 |
| WO | WO 02/067917 A1 | 9/2002 |
| WO | WO03/082081 A2 | 10/2003 |
| WO | WO-01-38344 A2 | 5/2004 |
| WO | WO-01-38344 A3 | 5/2004 |
| WO | WO-2004-050101 A2 | 6/2004 |
| WO | WO-2004-050101 A3 | 6/2004 |
| WO | WO 2004/069203 A2 | 8/2004 |
| WO | WO-2004-084883 A1 | 10/2004 |
| WO | WO-2004-098506 A2 | 11/2004 |
| WO | WO-2004-098506 A3 | 11/2004 |
| WO | WO-2004-059564 A1 | 6/2005 |

(Continued)

OTHER PUBLICATIONS

Noy et al. Interactions of retinol with binding proteins: studies with retinol-binding protein and with transthyretin. Biochemistry 1992, vol. 31, pp. 11118-11124.*

(Continued)

*Primary Examiner*—Mark L. Shibuya
*Assistant Examiner*—Shafiqul Haq
(74) *Attorney, Agent, or Firm*—Wilson Sonsini Goodrich & Rosati

(57) ABSTRACT

Described herein are methods and compositions for the detection of transthyretin (TTR), retinol binding protein (RBP) and retinol complex formation. The methods and compositions described herein also provide for the screening of modulators of retinol-RBP-TTR complex formation. Furthermore, the methods and compositions provide for therapeutic agents for the treatment and/or prevention of age-related macular degeneration and/or dystrophies.

3 Claims, 11 Drawing Sheets

FOREIGN PATENT DOCUMENTS

| | | |
|---|---|---|
| WO | WO-2005-077176 A1 | 8/2005 |
| WO | WO-2005-079774 A2 | 9/2005 |
| WO | WO-2005-087210 A2 | 9/2005 |
| WO | WO-2007-019503 A2 | 9/2005 |
| WO | WO-2007-019503 A3 | 9/2005 |
| WO | WO-2006-033734 A2 | 3/2006 |
| WO | WO-2006-033734 A3 | 3/2006 |
| WO | WO-2006-052860 A2 | 5/2006 |
| WO | WO-2006-052860 A3 | 5/2006 |

OTHER PUBLICATIONS

U.S. Appl. No. 60/578,324, filed Jun. 9, 2004, Robert R. Rando.

U.S. Appl. No. 60/567,604, filed Mar. 3, 2004, Robert R. Rando.

U.S. Appl. No. 60/545,456, filed Feb. 17, 2004, Robert R. Rando.

R. Allikmets et al., Mutation of the Stargardt Disease Gene (ABCR) in Age-Related Macular Degeneration, Science, vol. 277 (Sep. 19, 1997).

R. Allikmets, "Simple and Complex ABCR: Genetic Predisposition to Retinal Disease," Am. J. Hum. Genet. 67:793-799, Columbia University, NY (2000).

W. Baehr et al., "The retinoid cycle and retina disease," Vision Research 43 (2003) 2957-2958.

L. Baglietto et al., "Ocular Effects of Fenretinade, a Vitamin A Analog, in a Chemoprevention Trial of Bladder Cancer," Cancer Detection and Prevention 24(4):369-375 (2000).

M. L. Batten et al., "Lecithin-retinol Acyltransferase Is Essential for Accumulation of All-*trans*-Retinyl Esters in the Eye and in the Liver," J. of Biol. Chem., vol. 279, No. 11, Mar. 12, 2004, pp. 10422-10432.

D.R. Bergsma et al., "Vitamin A Receptors in Normal and Dystrophic Human Retina," Nature, vol. 265 (Jan. 6, 1977).

J.W. Berkow, M.D., "Subretinal Neovascularization in Senile Macular Degeneration," Am. J. of Ophthamology 97:143-147 (1984).

P.S. Bernstein, R.R. Rando, "In Vivo Isomerization of All-Trans-to 11-CIS-Retinoids in the Eye Occurs at the Alcohol Oxidation State," Biochemistry Oct. 21, 1986; 25(21):6473-6478.

D. Besch et al., "Inherited multifocal RPE-diseases: mechanisms for local dysfunction in global retinoid cycle gene defects," Vision Res. Dec. 2003;43(28):3095-108.

A. Bindewald, M.D. et al., "Visualization of Retinal Pigment Epithelial Cells in Vivo Using Digital High-Resolution Confocal Scanning Laser Ophthalmology," Am J. of Ophthalmology, Mar. 2004, pp. 556-558.

D. Bok, "New insights and new approaches toward the study of age-related macular degeneration," PNAS, Nov. 12, 2002, vol. 99 No. 23, 14619-14621.

R.C. Caruso, M.D. et al., "Effects of Fenretindate (4-HPR) on Dark Adaption," Arch. Ophthalmology, vol. 116 (Jun. 1998) pp. 739,760-763.

S. Chen et al., "Differentiation of Human Retinal Pigment Epithelial Cells into Neuronal Phenotype by N-(4-Hydroxyphenyl) Retinamide," J. Neurochem. (2003) 84, 972-981.

A.V. Cideciyan et al., "Mutations in ABCA4 result in accumulation of lipofuscin before slowing of the retinoid cycle: a reappraisal of the human disease sequence," Hum. Mol. Genet. 13(5) (2004) pp. 525-534.

J.W. Crabb et al., "Drusen Proteome Analysis: An Approach to the Etiology of Age-Related Macular Degeneration," PNAS (Nov. 12, 2002) vol. 99 No. 23, pp. 14682-14687.

F.P.M. Cremers et al., "Autosomal Recessive Retinitis Pigmentosa and Cone-Rod Dystophy Caused by Splice Site Mutations in the Stargardt's Disease Gene ABCR," Human Molecular Genetics (1998) vol. 7 No. 3, pp. 355-362.

R.K. Crouch and P. Goletz, "Fenretinide Does Not Block Visual Pigment Formation in the Rat," J. of Ocular Pharmacology, vol. 4 No. 3, 1988, pp. 253-256.

A. Decensi et al., "Effect of the Synthetic Retinoid Fenretinide on Dark Adaption and the Occular Surface," J. of the National Cancer Inst., vol. 86, No. 2 (Jan. 19, 1994) pp. 105-110.

A. Decensi et al., "Long-Term Effects of Fenretinide on Retinal Function," Eur. F. Cancer, vol. 33 No. 1, pp. 80-84 (1997).

F.C. Delori, "Autofluorescence method to measure macular pigment optical densities fluorometry and autofluorescence imaging," Archives of Biochem. And Biophysics 430 (2004) pp. 156-162.

S.E. Dew et al., "Effects of Pharmacological Retinoids on Several Vitamin A-Metabolizing Enzymes," Cancer Res. 53, 2965-2969 (Jul. 1, 1993).

F.L. Ferris, III, M.D. and R.D. Sperduto, M.D., "Standardized Illumination for Visual Activity Testing in Clinical Research," Am. J. of Ophthalmology 94:97098 (1982).

S.C. Finneman et al., "The Lipfuscin Component A2E Selectively Inhibits Phagolysosomal Degradation of Photoreceptor Phospholipid by the Retinal Pigment Epithelium," PNAS Mar. 19, 2002, vol. 99, No. 6, pp. 3842-3847.

F.Formelli et al., "Five-Year Administration of Fenretinide: Pharmacokinetics and Effects on Plasma Retinol Concentrations," J. of Clinical Oncology, vol. 11, No. 10 (Oct. 1993) pp. 2036-2042.

F. Formelli et al., "Plasma Retinol Level Reduction by Synthetic Retinoid Fenretinide: A One Year Follow-Up Study of Breast Cancer Patients," Cancer Res. 49, 6149-6152, Nov. 1, 1999.

F.T. Fraunfelder, M.D. et al., "Ocular Side Effects Possibly Associated with Isotretinoin Usage," Am. J. of Ophthalmology, Sep. 2001, pp. 299-305.

L. Garcia-Marcos and A. Schuster, "New perspectives for asthma treatment: Anti-leukotriene drugs," Pedatr. Allergy Immunol. 1999:10:77-88.

D.R. Gollapalli and R.R. Rando, "The Specific Binding of Retinoic Acid to RPE65 and Approaches to the Treatment of Macular Degeneration," PNAS, Jul. 6, 2004, vol. 101, No. 27, pp. 10030-10035.

M.H. Green and J.B. Green, "Model-Based Compartmental Analysis of Retinol Kinetics in Organs of Rats at Different Levels of Vitamin A Status," *Networks: New Trends in Research and Clinical Applications*, Livera, M.A., Packer, L., eds. Marcel-Dekker, Inc. New York 1993, pp. 185-204.

E.G. Gross, M.D. and M.A. Helfgott, M.D., "Retinoids and the Eye," Dermatologic Clinics, vol. 10, No. 3, Jul. 1992, pp. 521-531.

M. Hammer et al., "Spektrale Differenzieuring in Eigenfluoreszenzbildern des Augenhintergrunds von Patienten mit altersabhangiger Mankuladegerations," Online publiziert:vol. 101, No. 12, pp. 1189-1193 (Dec. 2004).

N.M. Haralampus-Grynaviski et al., "Spectroscopic and morphological studies of human retinal lipofuscin granules," PNAS, Mar. 18, 2003, vol. 100, No. 6., pp. 3179-3184.

F.G. Holz et al., "Flundus autofluorescence and development of geographic atrophy in age-related macular degeneration," Investigative Ophthalmol. And Visual Science 42 (2001) pp. 1051-1056.

T. Hultin et al., "N-(4-Hydroxyphenyl)-all trans-Retinamide Pharmacokineticsi n Female Rats and Mice," Drug, Metabolism and Disposition, vol. 14, No. 6, 1986, pp. 714-717.

L.J. Ignarro et al., "Endothelium-derived Relaxing Factor Produced and Released from Artery and Vein is Nitric Oxide," PNAS USA vol. 84, pp. 9265-9269 (Dec. 1987) Medical Sciences.

M.L. Kaiser-Kupper, M.D. et al., "Abnormal Retinal Function Associated With Fenretinide, a Synthetic Retinoid," Arch. Ophthalmol. vol. 104, Jan. 1996, pp. 69-70.

G. Karan et al., "Lipofuscin accumulation, abnormal electrophysiology, and photoreceptor degeneration inmutant ELOVL4 transgenic mice: a model for macular degeneration," PNAS USA, Mar. 15, 2005;102(11):4164-9.

M.L. Katz et al., "Dietary Vitamins A and E Influence Retinyl Ester Composition and Content of the Retinal Pigment Epithelium," Biochimica et Biophysica Acta 924 (1987) 432-441.

M.L. Katz et al., "Lipofuscin Autofluorescence: Evidence for Vitamin A Involvement in the Retina," Mechanisms of Ageing and Development, 39 (1987) 81-90, Elsevier Scientific Publishers Ireland Ltd.

M.L. Katz et al., "Relationship Between Dietary Retinol and Lipofuscin in the Retinal Pigment Epithelium," Mechanisms for Ageing and Development 35 (1986) 291-305, Elsevier Scientific Publishers Ireland Ltd.

M.L. Katz et al, "RPE65 gene mutation prevents development of autofluorescence in retinal pigment epithelial phagosomes," Mech. Ageing Dev. Apr. 2005;126(4):513-21.

W. Kedzierski et al., "Generation and Analysis of Transgenic Mice Expressing P216L-Substituted Rds/Peripherin in Rod Photoreceptors," Investigative Ophthalmology & Visual Science (Feb. 1997) vol. 38, No. 2, pp. 498-509.

S.R. Kim et al., "Rpe65 Leu450Met variant is associated with reduced levels of the retinal pigment epithelium lipofuscin fluorophores A2E and iso-A2E," PNAS Early Edition, www.pnas.org/cgi/doi/10.1073/pnas.0403499101 pp. 1-5.

B. J. Klevering et al., "Three Families Displaying the Combination of Stargardt's Disease with Cone-Rod Dystophy or Retinitis Pigmentosa," (2004) J. Ophthal. P.2003, by the Am. Acad. Of Ophthal. Published by Elsevier, Inc.

M. Kliffen et al., "Morphologic Changes in Age-Related Maculopathy," Microscopy Res. and Technique 36:106-122 (1997).

W.C. Law and R.R. Rando, "The Molecular Basic of Retinoid Acid Induced Night Blindness," Biochem. and Biophysical Res. Comm. vol. 161, No. 2, (Jun. 15, 1989) pp. 825-829.

R.A. Lewis et al.,"Genotype/Phenotype Analysis of a Photoreceptor-Specific ATP-Binding Cassette Transporter Gene, ABCR, in Stargardt Disease," Am. J. Hum. Genet. 64:422-434 (1999).

K.C. Lewis et al., "Effects of Chronic Administration of N-(4-hydroxyphenyl) Retinamide (4-HRP) in Rats on Vitamin A Metabolism in the Eye," Eur. J. Cancer, Vo.. 32A, pp. 1803-1808 (1996) (printed in Great Britain).

K.C. Lewis and J.F. Hochadel, "Retinoid Metabolism in the Prostate: Effects of Adminstration of the Synthetic Retinoid N-(4-Hydroxyphenyl) retinamide," Cancer Res. 59:5947-5955, Dec. 1, 1999.

C. Y. Li et al., "Solubilization of Retinoids by Bile Salt/Phospholipid Aggregates," Pharm. Res. vol. 13, No. 6, pp. 907-913 (1996).

G. Malpeli et al., "Retinoid binding to retinol-binding proteins and the interference with the interaction with transthyretin," Biochim. Biohphys. Acta May 2, 1996; 1294(1):48-54.

L. Mariani et al., "Chemoprevention of Breast Cancer with Fenretinide (4-HPR): Study of Long-Term Visual and Ophthalmologic Tolerability," Istituto Nazionale per lo Studi e la Cura dei Tumori, Milan: Istituto Nazionale Neurologico Carol Besta Milan; and European Institute of Oncology, Milan, Italy: Tumori 82:444-449 (1996).

A.D. Marmorstein et al., "Spectral Profiling of Autofluorescence Associated with Lipofuscin, Bruch's Membrane, and Sub-RPE Deposits in Normal and AMD Eyes," Investigative Ophthal. & Visual Science, Jul. 2002, vol. 43, No. 7, pp. 2435-2441.

N.L. Mata et al, "Biosynthesis of a major lipfuscin fluorophore in mice and humans with ABCR-mediated retinal and macular degeneration," PNAS, Jun. 20, 2000, vol. 97, No. 13, pp. 7154-7159.

G. McGwin et al., "The Association Between Statin Use and Age Related Maculopathy," Br. J. Ophthalmol. (2003);87:1121-1125.

M.R. Modiano et al., "Ocular Toxic Effects of Fenretinide," Brief Communications, vol. 82, No. 12, Jun. 20, 1990, p. 1063.

R.C. Moon et al., "n(4-Hydroxphenyl) Retinimide, a New Retinoid for Prevention of Breast Cancer in the Rat," Cancer Res. 39, 1339-1346 (Apr. 1979).

R.M.J. Palmer et al, "Nitric Oxide Release Accounts for the Biological Activity of Endothelium-derived Relaxing Factor," Nature, vol. 327 (Jun. 11, 1987) pp. 524-526.

R.A. Radu et al., "Treatment with Isotretinoin Inhibits Lipofuscin Accumulation in a Mouse Model of Recessive Stargardt's Macular Degeneration," PNAS vol. 100, No. 8, pp. 4742-4747 (Apr. 15, 2003).

R.A. Radu et al., "Light Exposure Stimulates Formation of A2E Oxinranes in a Mouse Model of Stargardt's Macular Degeneration," PNAS vol. 101, No. 16, pp. 5928-5933 (Apr. 20, 2004).

R.S. Rando, "The Biochemistry of the Visual Cycle," Chem. Rev. 2001, 101, 1881-1896.

R.R. Rando, "Small Molecule Approaches to the Management of Macular Degeneration by Short-Circuiting the Visual Cycle," http://www.techtransfer.harvard.edu/cgi-gin/TALSearch.cgi?full_report=1&case-2252 May 31, 2005.

H. Shaban and C. Richter, "A2E and Blue Light in the Retina: The Paradigm of Age-Related Macular Degeneration," Biol. Chem. vol. 383, pp. 537-545 (Mar./Apr. 2002).

H Shaban et al., "Phosphatidylglycerol Potently Protects Human Retinal Pigment Epithelial Cells Against Apoptosis Induced by A2E, a Compound Suspected to Cause Age-Related Macular Degeneration," Exp. Eye Res. (2002) 75,99-108.

P.A. Sieving et al., "Inhibition of the Visual Cycle in vivo by 13-cis Retinoic Acid Protects from Light Damage and Provides a Mechanism for Night Blindness in Isotretinoin Therapy," PNAS (Feb. 13, 2001) vol. 98 No. 4, 1834-1840.

R.F. Spaide, "Fundus autofluorescence and age-related macular degeneration," Ophthalmology 110 (2003) pp. 393-399.

J.R. Sparrow et al., "A2E-Epoxides Damage DNA in Retinal Pigment Epithelial Cells," J. of Biol. Chem. vol. 278, No. 20, May 16, 2003, pp. 18207-18213.

J.R. Sparrow et al., "A2E, a Lipofuscin Fluorophore, in Human Retinal Pigmented Epithelial Cells in Culture," Investigative Ophthal. & Visual Science, Nov. 1999, vol. 40, No. 12, pp. 2988-2995.

J.R. Sparrow et al., "DNA Is a Target of the Photodynamic Effects Elicited in A2E-Laden RPE by Blue-Light Illumination," Investigative Ophthal. & Visual Science, May 2003, vol. 44, No. 5, pp. 2245-2251.

J.R. Sparrow, "Therapy for macular degeneration: Insights from acne," PNAS, vol. 100, No. 8, Apr. 15, 2003, pp. 4353-4354.

R.L. Steinmetz et al., "Symptomatic Abnormalities of Dark Adaption in Patients with Age-Related Bruch's Membrane Change," Br. J. of Ophthal. 1993:77:549-554.

E.M. Stone et al., "Allelic Variation in ABCR Associated With Stargardt Disease but not Age-Related Macular Degeneration," Nature Genetics, vol. 20 (Dec. 1998).

R. Torrisi et al., "Factors Affecting Plasma Retinol Decline during Long-Term Administration of the Synthetic Retinoid Fenretinide in Breast Cancer Patients," Cancer, Epidemiology, Biomarkers & Prevention, vol. 3, 507-510 (Sep. 1994).

J.L. Ubels et al., "Biological Activity of N-(4-hydroxyphenyl) Retinamide-O-Glucuronide in Corneal and Conjunctival Cells of Rabbits and Humans," Current Eye Res. Recvd May 3, 1995, accepted Aug. 4, 1995, Oxford University Press.

S. J. Um et al., "Synthesis and Biological Activity ofNovel Retinamide and Retinoate Derivatives," Chem. Pharm. Bull 52(5) 501-506 (2004).

G.B. Villeneuve and T.H. Chan, "A Rapid, Mild and Acid-Free Procedure for the Preparation of Acyl Chlorides including Formyl Chloride," Tetrahedron Letters, vol. 38, No. 37, pp. 6489-6942 (1997).

S. Vogel et al., "Retinol-binding protein-deficient mice: biochemical basis for impaired vision," Biochemistry Dec. 24, 2002;41(51):15360-8.

J. Weng et al., "Insights into the Function of Rim Protein in Photoreceptors and Etiology of Stargardt's Disease from the Phenotype in ABCR Knockout Mice," Cell, vol. 98, 13-23 (Jul. 9, 1999).

M. Whittaker, et al., "Design and Therapeutic Application of Matrix Metalloproteinase Inhibitors," Chem. Rev. (1999) 99, 735-2776.

Areds Report No. 8, "A Randomized, Placebo-Controlled, Clinical Trial of High-Dose Supplementation with Vitamins C and E, Beta Caroten, and Zinc for Age-Related Macular Degeneration and Vision Loss," Arch. Ophthalmol. vol. 119 (Oct. 2001).

B. Wiggert et al., "Current Research Biochemistry Section," http://www.nei.nih.gov/intramural/biochem.asp#current Jun. 14, 2004.

National Eye Institute, Effect of DHA Supplements on Macular Function i Patients with Stargardt Macular Dystrophy and Stargardt-like Macular Dystrophy, http://www.clinicaltrials.gov/ct/show/NCT00060749 Aug. 18, 2004.

Virgo Publishing, "Vitamin,Mineral Combo Shows Promise for AMD,," http://www.naturalproductsinsider.com Oct. 12, 2001.

Nedelkov, D. and Nelson, R., "Delineattion of in vivo assembled multiprotein complexes via biomolecular interaction analysis mass spectrometry," Proteomics 2001, 1, 1441-1446.

Noy, N. et al., "Interactions of Retinol with Binding Proteins: Studies with Retinol-Binding Protein and with Transthyretin," Biochemistry 1992, 31, 11118-11124.

Zheng, W. et al., "Transthyretin, Thyroxine, and Retinol-Binding Protein in Human Cerebrospinal Fluid: Effect of Lead Exposure," Toxicological Sciences 61, 107-114 (2001).

Chen, S. et al., "Differentiation of cultured human retinal pigment epithelial (RPE) cells into neuronal phenotypes induced by fenretinide," Annual Meeting of the Association for Research in Vision and Ophthalmology, 2002, Abstract No. 4556.

Mata, N.L. et al., Effects of N-(4-hydroxyphenyl) retinamide on vitamin A homeostasis and A2E biosynthesis in abcr null mutant mice, Annual Meeting of the Association for Research in Vision and Ophthalmology, May 1, 2005, 46, 1744 (Abstract only).

Sharara, N.A. et al., "The potential clinical utility of fenretinide in the treatment of retinoblastoma; in vitro study," Annual Meeting of the Association for Research in Vision and Ophthalmology, 2003, Abstract No. 1581.

Caruso, R. et al., "Effects of Fenretinide (4-HPR) on Dark Adaptation," Arch. Ophthalmol. 116:759-763 (1998).

Gollapalli, D.R. and Rando, R.R., "The specific binding of retinoic acid to RPE65 and approaches to the treatment of macular degeneration," PNAS 101(27):10030-10035 (2004).

Katz, M.L. et al., "Relationship between dietary retinol and lipofuscin in the retinal pigment epithelium," Mechanisms of Ageing and Development 35:291-305 (1986).

Law, W.C. and Rando, R.R., "The Molecular Basis of Retinoic Acid Induced Night Blindness," Biochem. Biophys. Res. Comm. 161(2):825-829 (1989).

Lewis, K.C. et al., "Effects of Chronic Administration of N-(4-hydroxyphenyl)retinamide (4-HPR) in Rats on Vitamin A Metabolism in the Eye," Eur. J. Cancer 32A(10):1803-1808 (1996).

Lewis, K.C. et al., "Effects of N-(4-Hydroxyphenyl)retinamide Supplementation on Vitamin A Metabolism," Cancer Res. 54:4112-4117 (1994).

Malpeli, G. et al., "Retinoid binding to retinol-binding protein and the interference with the interaction with transthyretin," Biochimica et Biophysica Acta 1294:48-54 (1996).

Radu, R.A. et al., "Treatment with isotretinoin inhibits lipofuscin accumulation in a mouse model of recessive Stargardt's macular degeneration," PNAS 100(8):4742-4747 (2003).

Sparrow, J. R., "Therapy for macular degeneration: Insights from acne," PNAS 100(8):4353-4354 (2003).

Vogel, S. et al., "Retinol-Binding Protein-Deficient Mice: Biochemical Basis for Impaired Vision," Biochemistry 41:15360-15368 (2002).

Cogan, U. et al., "Binding Affinities of Retinol and Related Compounds to Retinol Binding Proteins," Eur. J. Biochem. 65:71-78 (1976).

Gollapalli, D.R. et al. "RPE65 Operates in the Vertebrate Visual Cycle by Stereospecifically Binding All-*trans*- Retinyl Esters," (Correction) Biochem. 43:7226 (2004).

Gollapalli, D.R. et al., "RPE65 Operates in the Vertebrate Visual Cycle by Stereospecifically Binding All-*trans*-Retinyl Esters," Biochem. 42:11824-11830 (2003).

Lakowicz, J.R., in *Principles of Fluorescence Spectroscopy*, 2$^{nd}$ ed. Kluwer, Academic/Plenum, New York (1999) pp. 53-55.

Noy, N. "Retinoid-binding proteins: mediators of retinoid action," Biochem. J. 348:481-495 (2000).

Sani, B.P. et al., "N-(4-hydroxyphenyl)retinamide: interactions with retinoid-binding proteins/receptors," Carcinogenesis 16(10):2531-2534 (1995).

Lovat, "GADD153 and 12-Lipoxygenase Mediate Fenretinide-induced Apoptosis of Neuroblastoma," Can. Res. 62:5158-5167 (2002).

Supplementary Search Report EP 05853359 dated Apr. 14, 2008.

\* cited by examiner

1. Excitation of RBP at 280nm (Ex1) produces emission at 340nm (Em1) and 450nm (Em2/donor). Em2 will be used as the donor fluorescence to excite the acceptor TTR-Alexafluor probe protein (see below)

2. Excitation of the TTR-Alexafluor probe (acceptor) via retinol fluorescence emission produces emission at 540nm which will be the final read-out wavelength (Em2).

E.

MODULATORS OF RETINOL-RETINOL BINDING PROTEIN (RBP)-TRANSTHYRETIN (TTR) COMPLEX FORMATION

CROSS-REFERENCE TO RELATED APPLICATIONS

This Application claims the benefit of U.S. Provisional Application Ser. No. 60/625,532 filed Nov. 4, 2004, U.S. Provisional Application Ser. No. 60/629,695, filed on Nov. 19, 2004, U.S. Provisional Application Ser. No. 60/660,904, filed on Mar. 11, 2005, U.S. Provisional Application Ser. No. 60/672,405, filed on Apr. 18, 2005, the disclosures of all of which are hereby incorporated by reference in their entirety.

FIELD OF THE INVENTION

The methods and compositions described herein are directed to the treatment of ophthalmic conditions.

BACKGROUND OF THE INVENTION

Retinoids are essential for maintenance of normal growth, development, immunity, reproduction, vision and other physiological processes. Conversely, abnormal production or processing of retinoids correlates with the manifestation of disease processes, including macular degeneration.

Macular degeneration is a group of eye diseases that is the leading cause of blindness for those aged 55 and older in the United States, affecting more than 10 million Americans. Some studies predict a six-fold increase in the number of new macular degeneration over the next decade, taking on the characteristics of an epidemic. Age-related macular degeneration or dystrophy, a particularly debilitating disease, leads to gradual loss of vision and eventually severe damage to the central vision.

To date, there is no effective cure for macular degeneration. Therefore, there is an urgent need to provide for assays that screen for therapeutic compositions to treat these diseases.

SUMMARY OF THE INVENTION

Described herein are methods and compositions for detecting agents which modulate the formation of a retinol-retinol binding protein (RBP)-transthyretin (TTR) complex. Also described herein are methods and compositions for detecting, quantitating, and/or monitoring the retinol-RBP-TTR complex. Also presented herein are treatment methods for ophthalmic conditions, including the wet and dry forms of the macular degenerations and dystrophies and geographic atrophy, comprising administration of a compound that modulates the formation of a retinol-retinol binding protein (RBP)-transthyretin (TTR) complex.

In one embodiment, the methods and compositions described herein provide for the detecting and/or quantitating of retinol-RBP-TTR complex formation in a sample comprising RBP, retinol and TTR comprising measuring the emission spectra of the complex, wherein at least some of the TTR further comprises a label. In one embodiment, the TTR is labeled with a fluorescence moiety. In another embodiment, the fluorescence moiety is an acceptor fluorescence moiety. Alternatively, the complex may be detected by fluorescence resonance energy transfer.

In further embodiments, the fluorescence moiety described herein absorbs at between 380 nm and 480 nm and emits at between 520 nm and 600 nm. In yet another embodiment, the fluorescence moiety may be chosen from the group consisting of: N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3- diazol-4-yl)amino)hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1, 8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl) pyridinium methanesulfonate, 1-(2,3-epoxypropyl)-4-(5-(4-methoxyphenyl)oxazol-2-yl)pyridinium trifluoromethanesulfonate, 1-(3-(succinimidyloxycarbonyl) benzyl)-4-(5-(4-methoxyphenyl)oxazol-2-yl)pyridinium bromide, 3-(4-carboxybenzoyl)quinoline-2-carboxaldehyde, 3-(2-furoyl)quinoline-2-carboxaldehyde or an ALEXA FLUOR® (fluorescent chemicals and biomolecule labeling kit) dye. In some embodiments, the sample may be illuminated so as to excite at least some of the amino acid groups of RBP.

Alternatively, the labeled TTR-RBP-retinol complex described herein may be excited at a wavelength of between 275 nm and 295 nm and the emission wavelength measured at between 330 nm and 650 nm. In other embodiments, the excitation wavelength for measuring the emission spectra may be between 315 and 345 nm, and the emission wavelength may be measured at between 525 and 600 nm.

In further embodiments, the labeled TTR may be immobilized on a solid support. Alternatively, the RBP may be immobilized on a solid support. The solid support described herein may comprise a nanoparticle. In other embodiments, the sample comprising the labeled TTR, RBP and retinol may be incubated in a microtiter plate or a microarray. In another embodiment, the sample described herein further comprises an inhibitor of retinol-RBP-TTR complex formation. Furthermore, in one embodiment the inhibitor is a retinyl derivative.

The methods and compositions described herein also provide for detecting and/or quantitating retinol-RBP-TTR complex formation in a sample, the sample comprising RBP, retinol and TTR attached to a fluorescence moiety, comprising incubating the sample under conditions sufficient to permit formation of a retinol-RBP-TTR complex and measuring the emission spectra of the complex. In another embodiment, the complex is detected by fluorescence resonance energy transfer, wherein the fluorescence moiety may absorb at between 380 nm and 480 nm and emit at between 520 nm and 600 nm. In other embodiments, the method described herein may provide an excitation wavelength for measuring the emission spectra at between 275 nm and 295 nm and the emission wavelength may be measured at between 330 nm and 650 nm. In yet another embodiment, the method described herein may provide an excitation wavelength for measuring the emission spectra at between 315 and 345 nm, and the emission wavelength may be measured at between 525 and 600 nm.

In further embodiments, the methods described herein provide for screening of modulators of retinol-RBP-TTR complex formation in a sample, the sample comprising at least one candidate modulator, labeled TTR, RBP and retinol, further comprising incubating the sample under conditions sufficient to permit formation of a retinol-RBP-TTR complex and measuring the emission spectra of the complex, wherein a change in the emission spectra of the complex after incubation of the candidate modulator indicates modulation of the retinol-RBP-TTR complex. In some embodiments, the TTR label is a fluorescence moiety. In other embodiments, the fluorescence moiety is an acceptor fluorescence moiety.

In yet another embodiment, the complex is detected by fluorescence resonance energy transfer. In other embodiments, the fluorescence moiety absorbs at between 380 nm and 480 nm and emits at between 520 nm and 600 nm. Alternatively, the fluorescence moiety may be chosen from the group consisting of: N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino)hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl)pyridinium methanesulfonate, 1-(2,3-epoxypropyl)-4-(5-(4-methoxyphenyl)oxazol-2-yl) pyridinium trifluoromethanesulfonate, 1-(3-(succinimidyloxycarbonyl)benzyl)-4-(5-(4-methoxyphenyl)oxazol-2-yl) pyridinium bromide, 3-(4-carboxybenzoyl)quinoline-2-carboxaldehyde, 3-(2-furoyl)quinoline-2-carboxaldehyde or an ALEXA FLUOR® dye.

In one embodiment, the sample may be illuminated with sufficient light to excite at least some of the amino acid moieties of the RBP. In another embodiment, at least some of the RBP of the sample forms the retinol-RBP-TTR complex in the sample.

In further embodiments, the excitation wavelength may be set at between 275 and 295 nm and the emission wavelength measured at between 330 and 650 nm. Alternatively, the excitation wavelength may be set at between 315 and 345 nm, and the emission wavelength measured at between 525 and 600 nm.

Furthermore, the methods described herein may comprise a labeled TTR immobilized on a solid support. Alternatively, the RBP may be immobilized on a solid support. In some embodiments, the solid support may be a nanoparticle. In other embodiments, the sample is incubated in a microtiter plate or microarray.

In further embodiments, the methods described herein provide for screening of modulators of retinol-RBP-TTR complex formation in a sample, the sample comprising at least one candidate modulator, a TTR attached to an acceptor fluorescence moiety, RBP and retinol, the method further comprising incubating the sample under conditions sufficient to permit formation of a retinol-RBP-TTR complex, and measuring the emission spectra of the sample, wherein a change in the emission spectra of the complex after incubation of the candidate modulator indicates modulation of the retinol-RBP-TTR complex.

In another embodiment, the methods described herein further provide for the screening of modulators of retinol-RBP-TTR complex formation in a sample, the sample comprising at least one candidate modulator, a TTR attached to an acceptor fluorescence moiety, RBP and retinol, the method further comprising incubating the sample under conditions sufficient to permit formation of a retinol-RBP-TTR complex, and measuring the emission spectra of the sample by fluorescence resonance energy transfer, wherein a change in the emission spectra of the complex after incubation of the candidate modulator indicates modulation of the retinol-RBP-TTR complex.

In one embodiment, the methods described herein further provide for the screening of modulators of retinol-RBP-TTR complex formation in a sample, the sample comprising at least one candidate modulator, a TTR attached to an acceptor fluorescence moiety, RBP and retinol, the method further comprising incubating the sample under conditions sufficient to permit formation of a retinol-RBP-TTR complex, adding at least one candidate inhibitor, and measuring the emission spectra of the sample, wherein a change in the emission spectra of the complex after incubation of the candidate modulator indicates modulation of the retinol-RBP-TTR complex.

In further embodiments, the methods described herein provide for screening of modulators of retinol-RBP-TTR complex formation in vivo, the method comprising injecting labeled TTR into a subject, introducing at least one candidate modulator into the subject, removing a biological sample from the subject, and measuring the emission spectra of the sample, wherein a change in the emission spectra of the complex after introduction of the candidate modulator indicates modulation of the retinol-RBP-TTR complex in vivo.

In another embodiment, the methods described herein provide for screening of modulators of retinol-RBP-TTR complex formation in vivo, the method comprising injecting TTR attached to an acceptor fluorescence moiety into a subject, introducing at least one candidate modulator into the subject, removing a biological sample from the subject, and measuring the emission spectra of the sample by fluorescence resonance energy transfer, wherein a change in the emission spectra of the complex after introduction of the candidate modulator indicates modulation of the retinol-RBP-TTR complex in vivo.

In further embodiments, a kit is provided for screening modulators of retinol-RBP-TTR complex formation comprising TTR and a means for labeling at least a portion of the TTR. In some embodiments, the kit further comprises retinol and RBP. In another embodiment, the kit provides for a fluorescent labeling means for labeling TTR. In other embodiments, the fluorescence label in the kit is an acceptor fluorescence moiety. In some embodiments, the acceptor fluorescence moiety in the kit is chosen from the group consisting of: N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino)hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl) pyridinium methanesulfonate, 1-(2,3-epoxypropyl)-4-(5-(4-methoxyphenyl)oxazol-2-yl)pyridinium trifluoromethanesulfonate, 1-(3-(succinimidyloxycarbonyl)benzyl)-4-(5-(4-methoxyphenyl)oxazol-2-yl) pyridinium bromide, 3-(4-carboxybenzoyl)quinoline-2-carboxaldehyde, 3-(2-furoyl)quinoline-2-carboxaldehyde or ALEXA FLUOR® dye.

In another embodiment, the acceptor fluorescence moiety of the kit absorbs at between 380 nm and 480 nm and emits at between 520 nm and 600 nm. Furthermore, the RBP and/or the labeled TTR of the kit may be immobilized on a solid support. In one embodiment, the solid support of the kit may be a nanoparticle.

In further embodiments, a labeled TTR molecule is provided, wherein the labeled TTR is attached to a fluorescence moiety. In some embodiments, the fluorescence moiety attached to the labeled TTR molecule may be chosen from the group consisting of: N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino)hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl) pyridinium methanesulfonate, 1-(2,3-epoxypropyl)-4-(5-(4-methoxyphenyl)oxazol-2-yl)pyridinium trifluoromethanesulfonate, 1-(3-(succinimidyloxycarbonyl)benzyl)-4-(5-(4-methoxyphenyl)oxazol-2-yl) pyridinium bromide, 3-(4-carboxybenzoyl)quinoline-2-carboxaldehyde, 3-(2-furoyl)quinoline-2-carboxaldehyde or ALEXA FLUOR® dye. In other embodiments, the acceptor fluorescence moiety attached to the labeled TTR molecule may absorb at between 380 nm and 480 nm and emit at between 520 nm and 600 nm. Furthermore, the labeled TTR may be attached to a solid support.

In further embodiments, a composition is provided comprising labeled TTR, RBP and retinol. In one embodiment, the methods and compositions further provide for a complex formed by the composition comprising labeled TTR, RBP and retinol.

In yet another embodiment, the composition further comprises at least one candidate therapeutic agent. In some embodiments, the candidate therapeutic agent is a small molecule, a polypeptide, a nucleic acid, or an antibody. In other embodiments, the candidate therapeutic agent is a retinyl derivative.

In further embodiments, the labeled TTR of the composition may be attached to a fluorescence moiety. In one embodiment, the fluorescence moiety may be N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino)hexanoic acid, succinimidyl 6-(N-(7-nitrobenz-2-oxa-1,3-diazol-4-yl) amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5methoxyphenyl)oxazol-2-yl)pyridinium methanesulfonate, 1-(2,3-epoxypropyl)-4-(5-(4-methoxyphenyl)oxazol-2-yl)pyridinium trifluoromethanesulfonate, 1-(3-(succinimidyloxycarbonyl)benzyl)-4-(5-(4-methoxyphenyl)oxazol-2-yl) pyridinium bromide, 3-(4-carboxybenzoyl)quinoline-2-carboxaldehyde, 3-(2-furoyl)quinoline-2-carboxaldehyde or an ALEXA FLUOR® dye. Alternatively, the fluorescence moiety of the composition may absorb at between 380 nm and 480 nm and emits at between 520 nm and 600 nm. In one embodiment, the labeled TTR is attached to a solid support.

In other embodiments, the methods described herein provide for identifying a therapeutic agent for the treatment of macular degenerations (including both the wet forms and dry forms of age-related macular degeneration) or dystrophies comprising incubating a sample comprising at least one candidate therapeutic agent, labeled TTR, RBP and retinol under conditions sufficient to permit formation of a retinol-RBP-labeled TTR complex, and measuring the emission spectra of the complex, wherein the candidate therapeutic agent decreases the emission spectra of the complex after incubation.

In some embodiments, the TTR label is a fluorescence moiety. In other embodiments, the fluorescence moiety is an acceptor fluorescence moiety. In some embodiments, the complex is detected by fluorescence resonance energy transfer. In other embodiments, the fluorescence moiety absorbs at between 380 nm and 480 nm and emits at between 520 nm and 600 nm. In one embodiment, the fluorescence moiety may be N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino)hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl) pyridinium methanesulfonate, 1-(2,3-epoxypropyl)-4-(5-(4-methoxyphenyl)oxazol-2-yl)pyridinium trifluoromethanesulfonate, 1-(3-(succinimidyloxycarbonyl)benzyl)-4-(5-(4-methoxyphenyl)oxazol-2-yl) pyridinium bromide, 3-(4-carboxybenzoyl)quinoline-2-carboxaldehyde, 3-(2-furoyl)quinoline-2-carboxaldehyde or an ALEXA FLUOR® dye. In one embodiment, the sample described herein is illuminated with sufficient light to excite at least some of the amino acid moieties of the RBP. Furthermore, in other embodiments at least some of the RBP in the sample forms the retinol-RBP-TTR complex.

In yet another embodiment, the excitation wavelength is between 275 nm and 295 nm and the emission wavelength is measured at between 330 nm and 650 nm. Alternatively, the excitation wavelength is between 315 and 345 nm, and the emission wavelength measured at between 525 and 600 nm. In some embodiments, the labeled TTR or the RBP is immobilized on a solid support. The solid support may also be a nanoparticle. In other embodiments, the sample is incubated in a microtiter plate or a microarray.

In further embodiments, the candidate therapeutic agent described herein is a small molecule, a polypeptide, a nucleic acid or an antibody. In other embodiments, the candidate therapeutic agent is a retinyl derivative. Alternatively, the retinyl derivative is N-(4-hydroxyphenyl)retinamide (also referred to herein as "HPR" or "fenretinide" or "4-hydroxyphenylretinamide" or "hydroxyphenyl retinamide"), N-(4-methoxyphenyl)retinamide ("MPR"; the most prevalent metabolite of HPR), or ethylretinamide.

In further embodiments, the methods described herein provide for identifying a therapeutic agent for the treatment of macular degenerations (including both the wet forms and dry forms of age-related macular degeneration) or dystrophies, wherein the method comprises incubating a sample comprising at least one candidate therapeutic agent, a TTR attached to an acceptor fluorescence moiety, RBP and retinol under conditions sufficient to permit formation of a TTR-RBP-retinol complex, and detecting the emission spectra of the sample by fluorescence resonance energy transfer, wherein the candidate therapeutic agent decreases the emission spectra of the complex after incubation.

In another embodiment, the methods described herein provide a modulator of the formation of a complex comprising retinol, RBP and TTR, wherein the modulator also modulates formation of a complex comprising retinol, RBP and labeled TTR. In one embodiment, the TTR is fluorescently labeled. In some embodiments, the complex of the modulator is in an in vitro sample. In other embodiments, the complex is in an in vivo sample. In one embodiment, the modulator further comprises a retinyl derivative. Alternatively, the retinyl derivative of the modulator is N-(4-hydroxyphenyl)retinamide ("HPR"), N-(4-methoxyphenyl)retinamide ("MPR"), or ethylretinamide.

In any of the aforementioned screening or detection or measuring or quantitation methods, strategies, compositions and kits, the following further embodiments may further be used singly or in any combination: (a) the sample has not been frozen; (b) the sample has been frozen for up to about two weeks; (c) the sample does not contain dimethylsulfoxide; (d) the sample contains up to about 8% dimethylsulfoxide; (e) the sample is performed using high-throughput methods; (f) the sample is contained within a well of a 384-well microtiter plate; (g) the mol % of label to tetrameric TTR is less than 5%; (h) the mol % of label to tetrameric TTR is less than 3%; (i) the mol % of label to tetrameric TTR is less than 2.5%; (j) the mol % of label to tetrameric TTR is less than 1.8%; (k) a compound of Formula (I) is used; (l) fenretinide is used; (m) a metabolite of fenretinide is used; (n) addition of a modulator of retinol-RBP-TTR formation to the sample results in a decrease the detected signal; (o) the detected signal from the retinol-RBP-TTR complex is measured as a function of the concentration of modulator; (p) the detected signal from the retinol-RBP-TTR complex is measured using a spectrometer; (r) the detected signal from the retinol-RBP-TTR complex is measured using a double-grating emission spectrometer; (s) the modulator of retinol-RBP-TTR complex formation reduces serum retinol levels when administered to a human; (t) the modulator of retinol-RBP-TTR complex formation reduces ocular levels of retinol when administered to a human; (u) the modulator of retinol-RBP-TTR complex formation reduces ocular levels of retinoids when administered to a human; (v) the modulator of retinol-RBP-TTR complex formation reduces ocular levels of A2E when administered to a human; or (w) the modulator of retinol-RBP-TTR complex formation is used to treat age-related macular degeneration (including both the wet forms and dry forms of age-related macular degeneration) in a human patient when administered to the human patient. In any of the aforementioned embodiments, the "TTR" can be labeled with a fluorophore.

In another embodiment are treatment methods for ophthalmic conditions, including macular degnerations (including both the wet forms and dry forms of age-related macular degeneration) and dystrophies and geographic atrophy, comprising administration of a compound that modulates the formation of a retinol-retinol binding protein (RBP)-transthyretin (TTR) complex. In further embodiments of the treatment methods, the compound that modulates the formation of a retinol-retinol binding protein (RBP)-transthyretin (TTR) complex is an all-trans retinyl derivative, wherein the all-trans retinyl derivative is administered at least once in an effective amount and has the structure of Formula (I):

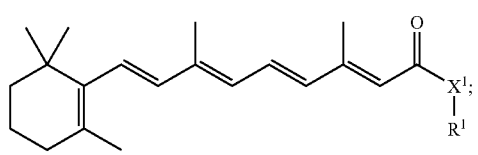

wherein $X_1$ is selected from the group consisting of $NR^2$, O, S, $CHR^2$; $R^1$ is $(CHR^2)_x$-$L^1$-$R^3$, wherein x is 0, 1, 2, or 3; $L^1$ is a single bond or —C(O)—; $R^2$ is a moiety selected from the group consisting of H, $(C_1$-$C_4)$alkyl, F, $(C_1$-$C_4)$fluoroalkyl, $(C_1$-$C_4)$alkoxy, —C(O)OH, —C(O)—$NH_2$, —$(C_1$-$C_4)$alkylamine, —C(O)—$(C_1$-$C_4)$alkyl, —C(O)—$(C_1$-$C_4)$fluoroalkyl, —C(O)—$(C_1$-$C_4)$alkylamine, and —C(O)—$(C_1$-$C_4)$alkoxy; and $R^3$ is H or a moiety, optionally substituted with 1-3 independently selected substituents, selected from the group consisting of $(C_2$-$C_7)$alkenyl, $(C_2$-$C_7)$alkynyl, aryl, $(C_3$-$C_7)$cycloalkyl, $(C_5$-$C_7)$cycloalkenyl, and a heterocycle, provided that $R^3$ is not H when both x is 0 and $L^1$ is a single bond; or an active metabolite, or a pharmaceutically acceptable prodrug or solvate thereof.

In further embodiments (a) $X^1$ is $NR^2$, wherein $R^2$ is H or $(C_1$-$C_4)$alkyl; (b) x is 0; (c) x is 1 and $L^1$ is —C(O)—; (d) $R^3$ is an optionally substituted aryl; (e) $R^3$ is an optionally substituted heteroaryl; (f) $X^1$ is NH and $R^3$ is an optionally substituted aryl, including yet further embodiments in which (i) the aryl group has one substituent, (ii) the aryl group has one substituent selected from the group consisting of halogen, OH, $O(C_1$-$C_4)$alkyl, $NH(C_1$-$C_4)$alkyl, $O(C_1$-$C_4)$fluoroalkyl, and $N[(C_1$-$C_4)$alkyl$]_2$, (iii) the aryl group has one substituent, which is OH, (v) the aryl is a phenyl, or (vi) the aryl is naphthyl; (g) the compound is

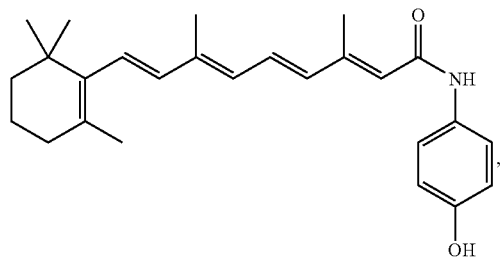

or an active metabolite, or a pharmaceutically acceptable prodrug or solvate thereof; (h) the compound is 4-hydroxyphenylretinamide, or a metabolite, or a pharmaceutically acceptable prodrug or solvate thereof; (i) the compound is 4-methoxyphenylretinamide, or (j) 4-oxo fenretinide, or a metabolite, or a pharmaceutically acceptable prodrug or solvate thereof.

In further embodiments, the administration of a compound of Formula (I) is used to treat ophthalmic conditions by lowering the levels of serum retinol in the body of a patient. In further embodiments (a) the effective amount of the compound is systemically administered to the mammal; (b) the effective amount of the compound is administered orally to the mammal; (c) the effective amount of the compound is intravenously administered to the mammal; (d) the effective amount of the compound is ophthalmically administered to the mammal; (e) the effective amount of the compound is administered by iontophoresis; or (f) the effective amount of the compound is administered by injection to the mammal.

In further embodiments the mammal is a human, including embodiments wherein (a) the human is a carrier of the mutant ABCA4 gene for Stargardt Disease or the human has a mutant ELOV4 gene for Stargardt Disease, or has a genetic variation in complement factor H associated with age-related macular degeneration, or (b) the human has an ophthalmic condition or trait selected from the group consisting of Stargardt Disease, recessive retinitis pigmentosa, geographic atrophy (of which scotoma is one non-limiting example), photoreceptor degeneration, dry-form AMD, recessive cone-rod dystrophy, exudative (or wet-form) age-related macular degeneration, cone-rod dystrophy, and retinitis pigmentosa. In further embodiments the mammal is an animal model for retinal degeneration.

In further embodiments, are methods comprising multiple administrations of the effective amount of the compound, including further embodiments in which (i) the time between multiple administrations is at least one week; (ii) the time between multiple administrations is at least one day; and (iii) the compound is administered to the mammal on a daily basis; or (iv) the compound is administered to the mammal every 12 hours. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In further embodiments are methods comprising administering at least one additional agent selected from the group consisting of an inducer of nitric oxide production, an anti-inflammatory agent, a physiologically acceptable antioxidant, a physiologically acceptable mineral, a negatively charged phospholipid, a carotenoid, a statin, an anti-angiogenic drug, a matrix metalloproteinase inhibitor, 13-cis-retinoic acid (including derivatives of 13-cis-retinoic acid), 11-cis-retinoic acid (including derivatives of 11-cis-retinoic acid), 9-cis-retinoic acid (including derivatives of 9-cis-retinoic acid), and retinylamine derivatives. In further embodiments:

(a) the additional agent is an inducer of nitric oxide production, including embodiments in which the inducer of nitric oxide production is selected from the group consisting of citrulline, ornithine, nitrosated L-arginine, nitrosylated L-arginine, nitrosated N-hydroxy-L-arginine, nitrosylated N-hydroxy-L-arginine, nitrosated L-homoarginine and nitrosylated L-homoarginine;

(b) the additional agent is an anti-inflammatory agent, including embodiments in which the anti-inflammatory agent is selected from the group consisting of a nonsteroidal anti-inflammatory drug, a lipoxygenase inhibitor, prednisone, dexamethasone, and a cyclooxygenase inhibitor;

(c) the additional agent is at least one physiologically acceptable antioxidant, including embodiments in which the physiologically acceptable antioxidant is selected from the group consisting of Vitamin C, Vitamin E, beta-carotene, Coenzyme Q, and 4-hydroxy-2,2,6,6-tetramethylpiperadine-N-oxyl, or embodiments in which (i) the at least one physiologically acceptable antioxidant is administered with the compound having the structure of Formula (I), or (ii) at least two physiologically acceptable antioxidants are administered with the compound having the structure of Formula (I);

(d) the additional agent is at least one physiologically acceptable mineral, including embodiments in which the physiologically acceptable mineral is selected from the group consisting of a zinc (II) compound, a Cu(II) compound, and a selenium (II) compound, or embodiments further comprising administering to the mammal at least one physiologically acceptable antioxidant;

(e) the additional agent is a negatively charged phospholipid, including embodiments in which the negatively charged phospholipid is phosphatidylglycerol;

(f) the additional agent is a carotenoid, including embodiments in which the carotenoid is selected from the group consisting of lutein and zeaxanthin;

(g) the additional agent is a statin, including embodiments in which the statin is selected from the group consisting of rosuvastatin, pitivastatin, simvastatin, pravastatin, cerivastatin, mevastatin, velostatin, fluvastatin, compactin, lovastatin, dalvastatin, fluindostatin, atorvastatin, atorvastatin calcium, and dihydrocompactin;

(h) the additional agent is an anti-angiogenic drug, including embodiments in which the the anti-angiogenic drug is Rhufab V2, Tryptophanyl-tRNA synthetase, an Anti-VEGF pegylated aptamer, Squalamine, anecortave acetate, Combretastatin A4 Prodrug, Macugen™, mifepristone, subtenon triamcinolone acetonide, intravitreal crystalline triamcinolone acetonide, AG3340, fluocinolone acetonide, and VEGF-Trap;

(i) the additional agent is a matrix metalloproteinase inhibitor, including embodiments in which the matrix metalloproteinase inhibitor is a tissue inhibitors of metalloproteinases, $\alpha_2$-macroglobulin, a tetracycline, a hydroxamate, a chelator, a synthetic MMP fragment, a succinyl mercaptopurine, a phosphonamidate, and a hydroxaminic acid;

(j) the additional agent is 13-cis-retinoic acid (including derivatives of 13-cis-retinoic acid), 11-cis-retinoic acid (including derivatives of 11-cis-retinoic acid), or 9-cis-retinoic acid (including derivatives of 9-cis-retinoic acid);

(k) the additional agent is a retinylamine derivative, including an all-trans-retinylamine derivative, a 13-cis-retinylamine derivative, a 11-cis-retinylamine derivative, or a 9-cis-retinylamine derivative;

(l) the additional agent is administered (i) prior to the administration of the compound having the structure of Formula (I), (ii) subsequent to the administration of the compound having the structure of Formula (I), (iii) simultaneously with the administration of the compound having the structure of Formula (I), or (iv) both prior and subsequent to the administration of the compound having the structure of Formula (I); or (m) the additional agent and the compound having the structure of Formula (I), are administered in the same pharmaceutical composition.

In further embodiments are methods comprising administering extracorporeal rheopheresis to the mammal. In further embodiments are methods comprising administering to the mammal a therapy selected from the group consisting of limited retinal translocation, photodynamic therapy, drusen lasering, macular hole surgery, macular translocation surgery, Phi-Motion, Proton Beam Therapy, Retinal Detachment and Vitreous Surgery, Scleral Buckle, Submacular Surgery, Transpupillary Thermotherapy, Photosystem I therapy, MicroCurrent Stimulation, anti-inflammatory agents, RNA interference, administration of eye medications such as phospholine iodide or echothiophate or carbonic anhydrase inhibitors, microchip implantation, stem cell therapy, gene replacement therapy, ribozyme gene therapy, photoreceptor/retinal cells transplantation, and acupuncture.

In further embodiments are methods comprising the use of laser photocoagulation to remove drusen from the eye of the mammal.

In further embodiments are methods comprising administering to the mammal at least once an effective amount of a second compound having the structure of Formula (I), wherein the first compound is different from the second compound.

In further embodiments, an apparatus capable of detecting and/or quantitating retinol-RBP-TTR complex formation is provided, wherein at least a portion of the TTR is fluorescently labeled.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the methods and compositions disclosed herein are set forth with particularity in the appended claims. A better understanding of the features and advantages will be obtained by reference to the following detailed description that sets forth illustrative embodiments, in which the principles disclosed herein are utilized, and the accompanying drawings of which:

DETAILED DESCRIPTION OF THE INVENTION

Reference will now be made in detail to embodiments of the methods and compositions disclosed herein. Examples of the embodiments are illustrated in the following Examples section.

Unless defined otherwise, all technical and scientific terms used herein have the same meaning as is commonly understood by one of skill in the art to which this invention belongs. All patents and publications referred to herein are incorporated by reference.

Figure 1:
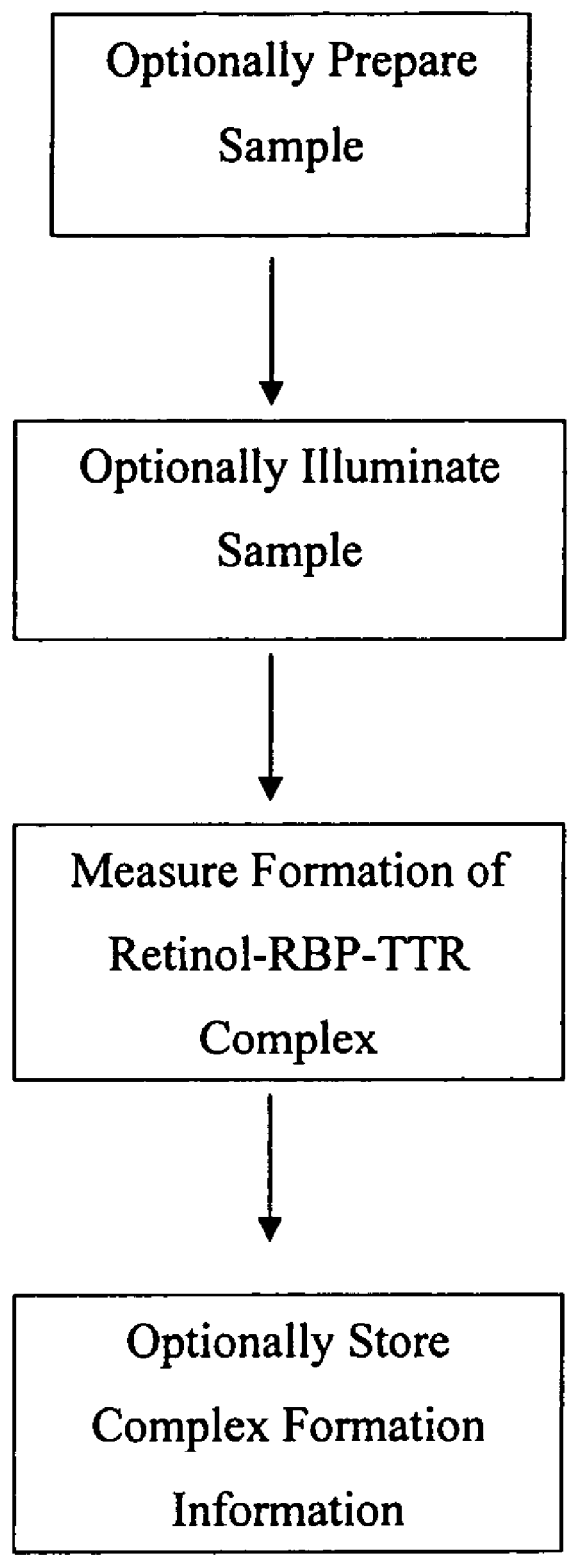
FIG. 1 illustrates a flowchart of one embodied method.

One of the methods for detecting agents which modulate the formation of a retinol-RBP-TTR complex is presented schematically in FIG. 1. An optional first step is the preparation of the sample. The sample can comprise purified components of the retinol-RBP-TTR complex; alternatively the sample can comprise a biological specimen including, but not limited to, blood, sera, tissue, mucus, saliva, tears, urine or feces. Further, the methods and compositions described herein may be used with test and/or laboratory animals, such as mice, rats, non-human primates, and the like. Such test and/or laboratory animals may be alive or dead. Such further preparations include homogenization of the biological specimens, including dispersal or suspension in another media, and the like. Further, the samples may include or be derived from cultured cells or from tissue banks, or from storage centers.

After optionally preparing the sample, complex formation is detected, for example, by illumination with light. The methods and devices described herein are not limited by the type or source of light, that is, the light may originate, by way of example only, from a lamp, laser, or light-emitting diode. The light may be pulsed (in any sequence) or continuous; further the light may be coherent or non-coherent; further the light may be polarized or non-polarized; further the light may pass through filters (including, but not limited to band-pass filters), blocking (e.g.; spatial filtering) and/or focusing devices; further the light may illuminate all or only a portion of the sample. The wavelength range or ranges used for illuminating the sample depend upon the fluorescent compound or compounds to be detected, further detail is provided herein for specific compounds. Preferably, the wavelength(s) of light used in the illuminating step should excite the fluorescent compound so as to emit a fluorescence signal that can be subsequently detected and/or measured. In addition, the wavelength range used for illumination may also include wavelengths that are not well absorbed (if at all) by the fluorescence compounds of interest; such light may be used as a reference signal or for background subtraction. However, the use of such a reference or background signal is not required by the methods and devices described herein. In addition, the absorbance of the illuminating light may also be measured and used separately or in combination with the fluorescence signal measured and/or detected in the detection step. Such an absorbance signal may be diagnostic for a particular fluorescent compound, as described elsewhere herein. The key requirement for the illumination step is that the fluorescent compound or compounds to be detected absorb at least a portion of the light applied to the sample. The use of a microprocessor may also be used to control the illumination step. In any sample, there may be more than one type of fluorescent compound; if more than one type of fluorescent compound is presented, then the illuminating light may be provided so as to be absorbed by only one type of compound or by multiple types of compounds.

After illuminating the sample, the fluorescence emitted from the fluorescent compounds in the sample is detected. Such emitted fluorescence may be detected by any number of methods, or a combination of methods. For example, the fluorescence signal may be detected at only one wavelength, at different wavelengths, at a range of wavelengths, or over multiple ranges of wavelengths. If a specific fluorescence is being detected and/or measured, then one of the methods described herein examines a specific range of wavelengths that corresponds to the major component The information or data acquired from the detection step may be stored temporarily or permanently in a variety of media, including by way of example only, film, computer memory or any other form of archival material. Such recordkeeping and/or storage of information and data is generally associated with laboratory practices, and/or patient diagnosis and treatment, as well as for testing the effectiveness of a modulator or therapeutic agent (in vivo or in vitro). By storing or archiving such information, one of skill in the art can also create a temporal analysis of the sample. Furthermore, the archived information, data or images can be further processed (e.g., magnified, enriched, deconvoluted, pseudocolored, quantitated) as desired.

The optional sample preparation, the illumination of the sample, the detection of fluorescence and the optional storage of information can be considered one detection cycle. As such, it is contemplated herein the repetition of this detection cycle on a sample. Certainly, if the sample is already prepared, it may not be necessary to re-prepare the sample, especially if the time interval between detection cycles is short (e.g., less than 10 seconds, less than one minute, less than 5 minutes or less than one hour or even less than one day). By way of example only, it may be necessary to repeat a detection cycle to ensure the accuracy of the measurements, in which case, the time interval between detection cycles may be relatively short. If the interval between detection cycles is longer, it may be necessary to store the sample. In addition, if the sample is being tested with a therapeutic agent or a potential modulator (e.g., in the testing and/or design of a new drug), the interval between detection cycles may be used to provide further manipulation to the sample. The time between detection cycles may be less than 10 seconds, less than one minute, more than 5 minutes, more than one hour, or even more than one day. The duration of time between detection cycles and the number of times the detection cycle is repeated is within the discretion of one of skill in the art. In any case, the duration of time between detection cycles does not have to be uniform and may be a combination of multiple repeat cycles.

The information collected from a detection cycle or cycles may be optionally used for a number of purposes in which the absorbance and/or fluorescence detected from a sample is used as a surrogate marker and/or risk factor for the status of a sample. Non-limiting examples include (a) measuring the effectiveness of a therapeutic candidate for a relevant ophthalmic disease or condition (including the retinal and/or macular degenerations (including both the wet forms and dry forms of age-related macular degeneration) or dystrophies) in an in vitro sample or an in vivo sample (including the injection of components of the retinol-RBP-labeled TTR into a living laboratory animal, including a rodent or an ABCA4 knockout mouse) by measuring changes in the amount of fluorescent compound(s) in a sample following administration of the therapeutic candidate to the sample; and (b) measuring the effectiveness of a treatment for a relevant ophthalmic disease or condition (including the retinal and/or macular degenerations (including both the wet forms and dry forms of age-related macular degeneration) or dystrophies) in an in vivo sample (including the injection of components of the retinol-RBP-labeled TTR into a living laboratory animal, including a rodent or an ABCA4 knockout mouse) by measuring changes in the amount of fluorescent compound(s) in a sample following administration of a treatment to the laboratory animal.

As used herein, the term "ABCA4 gene" refers to a gene encoding the rim protein or RmP. The ABCA4 gene is also known as the ABCR gene.

As used herein, the term "anti-oxidant" refers to a synthetic or natural substance that can prevent, delay or otherwise inhibit the oxidation of a compound or biological substance.

As used herein, the term "deconvoluting" refers to the process of converting data, information and/or images into (at least in part) constituent components. For example, a fluorescence or absorbance spectrum that features a complex wave form can be mathematically deconvoluted into the separate absorbance or fluorescence peaks that comprise the complex wave form. Suitable mathematical procedures and algorithms are well-known in the art, and suitable software packages for deconvoluting data, information and/or images are commercially available.

As used herein, the term "disruption of the visual cycle" or the like refers to any means for modulating the activity, directly or indirectly, of at least one enzyme involved in the visual cycle.

As used herein, the term "dispersing" refers to suspending a substance in another medium. Dispersing can include steps for homogenizing, fractionating, breaking up, fluidizing or decreasing the size of a substance in order to facilitate the suspending step.

As used herein, a retinyl derivative refers to a compound that can be produced by reacting one of the various cis or trans retinal isomers with another compound or series of compounds.

As used herein, the term "age-related macular degeneration or dystrophy" or "ARMD" refers to a debilitating disease, which include wet and dry forms of ARMD. The dry form of ARMD, which accounts for about 90 percent of all cases, is also known as atrophic, nonexudative, or drusenoid (age-related) macular degeneration. With the dry form of ARMD, drusen typically accumulate in the retinal pigment epithelium (RPE) tissue beneath/within the Bruch's membrane. Vision loss can then occur when drusen interfere with the function of photoreceptors in the macula. The dry form of ARMD results in the gradual loss of vision over many years. The dry form of ARMD can lead to the wet form of ARMD. The wet form of ARMD, also known as exudative or neovascular (age-related) macular degeneration, can progress rapidly and cause severe damage to central vision. The macular dystrophies include Stargardt Disease, also known as Stargardt Macular Dystrophy or Fundus Flavimaculatus, which is the most frequently encountered juvenile onset form of macular dystrophy.

As used herein, the term "mammal" refers to all mammals including humans. Mammals include, by way of example only, humans, non-human primates, cows, dogs, cats, goats, sheep pigs, rats, mice and rabbits.

As used herein, the term "biological sample" refers to the eyes, plasma, blood, urine, feces, tissue, mucus, tears or saliva of a mammal.

As used herein, the term "effective amount" refers to the total amount of the therapeutic agent in the pharmaceutical formulation or method that is sufficient to show a meaningful subject or patient benefit.

As used herein, the term "measuring the emission fluorescence" refers to any means for either (a) detecting the presence of a fluorescent compound by detecting the presence of its fluorescence following excitation by some form of illumination, (b) measuring the amount of a fluorescent compound by measuring the intensity (absolute or relative) of the fluorescence emitted by the fluorescent compounds in a sample following excitation by some form of illumination, and (c) a combination of the above.

As used herein, the term "emission spectra" refers to a plot of relative intensity of emitted radiation as a function of wavelength.

As used herein, the term "emission wavelength" refers to the maximal wavelength or wavelength range of emitted radiation upon excitation by light energy.

As used herein, the term "excitation wavelength" refers to the wavelength of an external energy source equivalent to the photon of energy $h\nu_{EX}$ supplied by the external source, such as an incandescent lamp or a laser, and absorbed by the fluorophore, creating an excited electronic singlet state.

As used herein, the term "fluorescence moiety" refers to a fluorescent species or substance.

As used herein, the term "acceptor fluorescence moiety" refers to a fluorescent species or substance in FRET detection which accepts a donor electron from a donor fluorescent species.

As used herein, the term "fluorescence resonance energy transfer" or "FRET" refers to the transfer of energy between an acceptor and donor species, wherein the absorption spectrum of the acceptor species overlaps the emission spectrum of the donor species.

As used herein, the term "ophthalmic disease or condition" refers to any disease or condition involving the eye or related tissues. Non-limiting examples include diseases or conditions involving degeneration of the retina and/or macula, including the retinal and/or macular dystrophies and the retinal and/or macular degenerations.

As used herein, the term "immobilized" refers to the covalent or non-covalent attachment of a chemical or biological species to a support.

As used herein, the term "primate" refers to the highest order of mammals; includes man, apes and monkeys.

As used herein, the term "risk" refers to the probability that an event will occur.

The Visual Cycle

The vertebrate retina contains two types of photoreceptor cells. Rods are specialized for vision under low light conditions. Cones are less sensitive, provide vision at high temporal and spatial resolutions, and afford color perception. Under daylight conditions, the rod response is saturated and vision is mediated entirely by cones. Both cell types contain a structure called the outer segment comprising a stack of membranous discs. The reactions of visual transduction take place on the surfaces of these discs. The first step in vision is absorption of a photon by an opsin-pigment molecule, which involves 11-cis to all-trans isomerization of the retinal chromophore. Before light sensitivity can be regained, the resulting all-trans-retinal must dissociate from the opsin apoprotein and isomerize to 11-cis-retinal.

Further information regarding the anatomical organization of the vertebrate eye, the visual cycle for regeneration of rhodopsin, and the biogenesis of A2E-oxiranes is provided in U.S. Provisional Pat. App. No. 60/582,293, filed Jun. 23, 2004, U.S. Provisional Pat. App. No. 60/602,675, filed Aug. 18, 2004 and U.S. Provisional Pat. App. No. 60/622,213, filed Oct. 25, 2004, the contents of which are incorporated by reference in their entirety.

Macular or Retinal Degeneration

As discussed above, macular degeneration (also referred to as retinal degeneration) is a disease of the eye that involves deterioration of the macula, the central portion of the retina. Approximately 85% to 90% of the cases of macular degeneration are the "dry" (atrophic or non-neovascular) type.

In "dry" macular degeneration, the deterioration of the retina is associated with the formation of small yellow deposits, known as drusen, under the macula. This phenomena leads to a thinning and drying out of the macula. The location and amount of thinning in the retinal caused by the drusen directly correlates to the amount of central vision loss. Degeneration of the pigmented layer of the retina and photoreceptors overlying drusen become atrophic and cause a slow of central vision. This often occurs over a decade or more.

Most people who lose vision from age related macular degeneration have "wet" macular degeneration. In "wet" (neovascular) macular degeneration, abnormal blood vessels from the choroidal layer of the eye, known as subretinal neovascularization grow under the retina and macula. These blood vessels tend to proliferate with fibrous tissue, and bleed and leak fluid under the macula, causing the macula to bulge or move and distort the central vision. Acute vision loss occurs as transudate or hemorrhage accumulates in and beneath the retina. Permanent vision loss occurs as the outer retina becomes atrophic or replaced by fibrous tissues.

Stargardt Disease

Stargardt Disease is a macular dystrophy that manifests as a recessive form of macular degeneration with an onset during childhood. See e.g., Allikmets et al., Science, 277:1805-07 (1997). Stargardt Disease is characterized clinically by progressive loss of central vision and progressive atrophy of the RPE overlying the macula. Mutations in the human ABCA4 gene for RmP are responsible for Stargardt Disease. Early in the disease course, patients show delayed dark adaptation but otherwise normal rod function. Histologically, Stargardt Disease is associated with deposition of lipofuscin pigment granules in RPE cells.

Besides Stargardt Disease, mutations in ABCA4 have been implicated in recessive retinitis pigmentosa, recessive cone-rod dystrophy, and non-exudative age-related macular degeneration (AMD), see e.g., Lewis et al., Am. J. Hum. Genet., 64:422-34 (1999), although the prevalence of ABCA4 mutations in AMD is still uncertain. See Allikmets, Am. J. Hum. Gen., 67:793-799 (2000). Similar to Stargardt Disease, these diseases are associated with delayed rod dark-adaptation. Lipofuscin deposition in RPE cells is also seen prominently in AMD, see Kliffen et al., Microsc. Res. Tech., 36:106-22 (1997) and some cases of retinitis pigmentosa and cone-rod dystrophy.

An eye doctor examining a patient at this stage may note the presence of these drusen, even though most people have no symptoms. When drusen have been noted on examination, monitoring will be needed over time. Many people over the age of 60 will have some drusen.

Modulation of Retinol-Retinol Binding Protein (RBP)-Transthyretin (TTR) Binding

The methods and compositions described herein are useful for the detection and screening of modulators of retinol binding to retinol binding protein (RBP), and the transport complex retinol-RBP-TTR. Vitamin A (all-trans retinol) is a vital cellular nutrient which cannot be synthesized de novo and therefore must be obtained from dietary sources. Following digestion, retinol in food material is transported to the liver bound to lipid aggregates. See Bellovino et al., Mol. Aspects Med., 24:411-20 (2003). Once in the liver, retinol forms a complex with retinol binding protein (RBP) and is then secreted into the blood circulation. Before the retinol-RBP holoprotein can be delivered to extra-hepatic target tissues, such as the eye, it must bind with transthyretin (TTR). Zanotti and Berni, Vitam. Horm., 69:271-95 (2004). It is this secondary complex which allows retinol to remain in the circulation for prolonged periods. Association with TTR facilitates RBP release from hepatocytes, and prevents renal filtration of the RBP-retinol complex. The retinol-RBP-TTR complex is delivered to target tissues where retinol is taken up and utilized for various cellular processes. Delivery of retinol to cells through the circulation by the RBP-TTR complex is the major pathway through which cells and tissue acquire retinol.

Retinol binding protein, or RBP, is a single polypeptide chain, with a molecular weight of approximately 21 kD. RBP has been cloned and sequenced, and its amino acid sequence determined. Colantuni et al., Nuc. Acids Res., 11:7769-7776 (1983). The three-dimensional structure of RBP reveals a specialized hydrophobic pocket designed to bind and protect the fat-soluble vitamin retinol. Newcomer et al., EMBO J., 3:1451-1454 (1984). In in vitro experiments, cultured hepatocytes have been shown to synthesize and secrete RBP. Blaner, W. S., Endocrine Rev., 10:308-316 (1989). Subsequent experiments have demonstrated that many cells contain mRNA for RBP, suggesting a widespread distribution of RBP synthesis throughout the body (Blaner (1989)). Most of the RBP secreted by the liver contains retinol in a 1:1 molar ratio, and retinol binding to RBP is required for normal RBP secretion.

In cells, RBP tightly binds to retinol in the endoplasmic reticulum, where it is found in high concentrations. Binding of retinol to RBP initiates a translocation of retinol-RBP from endoplasmic reticulum to the Golgi complex, followed by secretion of retinol-RBP from the cells. RBP secreted from hepatocytes also assists in the transfer of retinol from hepatocytes to stellate cells, where direct secretion of retinol-RBP into plasma takes place.

In plasma, approximately 95% of the plasma RBP is associated with transthyretin (TTR) in a 1:1 mol/mol ratio, wherein essentially all of the plasma vitamin A is bound to RBP. TTR is a well-characterized plasma protein consisting of four identical subunits with a molecular weight of 54,980. The full three-dimensional structure, elucidated by X-ray diffraction, reveals extensive β-sheets arranged tetrahedrally. Blake et al., J. Mol. Biol., 121:339-356 (1978). A channel runs through the center of the tetramer in which is located two binding sites for thyroxine. However, only one thyroxine molecule appears to be bound normally to TTR due to negative cooperativity. The complexation of TTR to RBP-retinol is thought to reduce the glomerular filtration of retinol, thereby increasing the half-life of retinol and RBP in plasma by about threefold. See e.g., Blomhoff(1994).

Retinol uptake from its complexed retinol-RBP-TTR form into cells occurs by binding of RBP to cellular receptors on target cells. This interaction leads to endocytosis of the RBP-receptor complex and subsequent release of retinol from the complex, or binding of retinol to cellular retinol binding proteins (CRBP), and subsequent release of apoRBP by the cells into the plasma. Other pathways contemplate alternative mechanisms for the entry of retinol into cells, including uptake of retinol alone into the cell. See Blomhoff(1994) for review.

A2E, the major fluorophore of lipofuscin, is formed in macular or retinal degeneration or dystrophy, including age-related macular degeneration and Stargardt Disease, due to excess production of the visual-cycle retinoid, all-trans-retinaldehyde, a precursor of A2E. Reduction of vitamin A and all-trans retinaldehyde in the retina, therefore, would be beneficial in reducing A2E and lipofuscin build-up, and treatment of age-related macular degeneration. Studies have confirmed that reducing serum retinol may have a beneficial effect of reducing A2E and lipofuscin in RPE. For example, animals maintained on a vitamin A deficient diet have been shown to demonstrate significant reductions in lipofuscin accumulation. Katz et al., Mech. Ageing Dev., 35:291-305 (1986); Katz et al., Mech. Ageing Dev., 39:81-90 (1987); Katz et al., Biochim. Biophys. Acta, 924:432-41 (1987). Further evidence that reducing vitamin A levels may be beneficial in the progression of macular degeneration and dystrophy was shown by Radu and colleagues, where reduction in ocular vitamin A levels resulted in reductions in both lipofuscin and A2E. Radu et al., Proc. Natl. Acad. Sci. USA, 100:4742-7 (2003); Radu et al., Proc. Natl. Acad. Sci. USA, 101:5928-33 (2004).

Administration of the retinoic acid analog, N-4-(hydroxyphenyl)retinamide, has been shown to cause profound reductions in serum retinol and RBP. Formelli et al., Cancer Res. 49:6149-52 (1989); Formelli et al., J. Clin Oncol., 11:2036-42 (1993); Torrisi et al., Cancer Epidemiol. Biomarkers Prev., 3:507-10 (1994). In vitro studies have demonstrated that HPR interferes with the normal interaction of TTR with RBP. Malpeli et al., Biochim. Biophys. Acta 1294: 48-54 (1996); Holven et al., Int. J. Cancer 71:654-9 (1997).

Modulators (e.g. HPR) that inhibit delivery of retinol to cells either through interruption of binding of retinol to RBP or the RBP-TTR complex, or the increased renal excretion of retinol and RBP, therefore, would be useful in decreasing serum levels, and buildup of retinol and its derivatives in target tissues such as the eye. The methods and compositions described herein provide for the detection and screening of such modulators, and provides kits for the screening of retinol binding modulators.

One embodiment provides for retinol, retinol binding protein (RBP) and transthyretin (TTR) for the monitoring of retinol-RBP-TTR complex formation. Retinol, or vitamin A, binds to various binding proteins, including retinol binding protein, for transport to target organs such as the eye. Vitamin A is a generic term which may designate any compound possessing the biological activity, including binding activity, of retinol. One retinol equivalent (RE) is the specific biologic activity of 1 μg of all-trans retinol (3.33 IU) or 6 μg (10 IU) of beta-carotene. Beta-carotene, retinol and retinal (vitamin A aldehyde) all possess effective and reliable vitamin A activity.

Some examples of potential modulators of retinol-RBP-TTR complex formation include derivatives of vitamin A, such as tretinoin (all trans-retinoic acid) and isotretinoin (13-cis-retinoic acid), which are used in the treatment of acne and certain other skin disorders. Other derivatives include fenretinide (N-(4-hydroxyphenyl)retinamide), MPR and ethylretinamide. In some aspects of the methods and compositions disclosed herein, it is contemplated that derivatives of retinol, retinyl derivatives and related retinoids may be used alone, or in combination with, other derivatives of retinol or related retinoids.

Fenretinide (hereinafter referred to as hydroxyphenyl retinamide) is particularly useful in the compositions and methods disclosed herein. As will be explained below, fenretinide may be used as a modulator of retinol, RBP and TTR complex formation. In some aspects of the methods and compositions described herein, derivatives of fenretinide may be used instead of, or in combination with, fenretinide. As used herein, a "fenretinide derivative" refers to a compound whose chemical structure comprises a 4-hydroxy moiety and a retinamide. The most prevalent metabolite of HPR is MPR, a compound that can also reduce serum retinol levels. As such, reference herein to HPR or fenretinide includes the metabolite MPR.

In some embodiments, derivatives of fenretinide that may be used include, but are not limited to, C-glycoside and arylamide analogues of N-(4-hydroxyphenyl) retinamide-O-glucuronide, including but not limited to 4-(retinamido)phenyl-C-glucuronide, 4-(retinamido)phenyl-C-glucoside, 4-(retinamido)phenyl-C-xyloside, 4-(retinamido)benzyl-C-glucuronide, 4-(retinamido)benzyl-C-glucoside, 4-(retinamido)benzyl-C-xyloside; and retinoyl β-glucuronide analogues such as, for example, 1-(β-D-glucopyranosyl) retinamide and 1-(D-glucopyranosyluronosyl) retinamide, described in U.S. Pat. Nos. 5,516,792, 5,663,377, 5,599,953, 5,574,177, and Bhatnagar et al., Biochem. Pharmacol., 41:1471-7 (1991), each incorporated herein by reference.

In other embodiments, other vitamin A derivatives may be used, including those disclosed in U.S. Pat. No. 4,743,400, incorporated herein by reference. These retinoids include, for example, all-trans retinoyl chloride, all-trans-4-(methoxyphenyl) retinamide, 13-cis-4-(hydroxyphenyl)retinamide and all-trans-4-(ethoxyphenyl) retinamide. U.S. Pat. No.

4,310,546, incorporated herein by reference, describes N-(4-acyloxyphenyl)-all-trans retinamides, such as, for example, N-(4-acetoxyphenyl)-all-trans-retinamide, N-(4-propionyloxyphenyl)-all-trans-retinamide and N-(4-n-butyryloxyphenyl-)-all-trans-retinamide, all of which are contemplated for use in certain embodiments.

Other vitamin A derivatives or metabolites, such as N-(1H-tetrazol-5-yl)retinamide, N-ethylretinamide, 13-cis-N-ethylretinamide, N-butylretinamide, etretin (acitretin), etretinate, tretinoin (all-trans-retinoic acid) or isotretinoin (13-cis-retinoic acid) may be contemplated for use in certain embodiments. See U.S. Provisional Patent Applications Nos. 60/582,293 and 60/602,675; see also Turton et al., Int. J. Exp. Pathol., 73:551-63 (1992), all herein incorporated by reference).

Other potential modulators include, but are not limited to, non-steroidal antiinflammatory drugs, including, by way of example only, flufenamic acid, mefenamic acid, meclofenamic acid, diflunisal, diclofenac, flurbiprofen, fenoprofen, and indomethacin. Other potential modulators include, but are not limited to, biaryls, biarylamines, stilbenes, and dibenzofurans. Further exemplary potential modulators can be found in Purkey, et al., Proc. Natl. Acad. Sci., 98:5566-71 (2001), which is hereby incorporated by reference in its entirety.

Other potential modulators include small molecules, polypeptides, nucleic acids and antibodies. For example, the methods and compositions described herein may be used to screen small molecule libraries, nucleic acid libraries, peptide libraries or antibody libraries in conjunction with the teachings disclosed herein. Methods for screening libraries, such as combinatorial libraries and other libraries disclosed above, can be found in U.S. Pat. Nos. 5,591,646; 5,866,341; and 6,343,257, which are hereby incorporated by reference in its entirety.

In one embodiment, the methods and compositions disclosed herein can be applied to the labeling of a retinol-RBP-TTR complex member. In this approach, labels, such as enzymes, fluorescers, radiolabels, chemiluminescers, specific binding pairs, such as avidin and biotin, ligands, and antibodies, e.g. digoxin and antidigoxin, and the like, where the protein of interest, for example TTR, may be labeled with the labels indicated above. In one embodiment, a fluorophore is attached to the TTR. In some embodiments, the proteins are labeled with a fluorophore with an absorbance spectra of between 380 and 480 nm, and an emission spectra of between 520 nm and 600 nm. In another embodiment, the proteins may be labeled with a fluorophore with an absorbance spectra between 410 and 490 nm, and an emission spectra of between 530 and 595 nm. One of ordinary skill in the art will recognize that other fluorophore moieties may be used in conjunction with the teachings disclosed herein in order to identify modulators of retinol-RBP-TTR complex formation.

Representative flurophores that may be used include N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino) hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl)pyridinium methanesulfonate, 1-(2,3-epoxypropyl)-4-(5-(4-methoxyphenyl) oxazol-2-yl)pyridinium trifluoromethanesulfonate, 1-(3-(succinimidyloxycarbonyl)benzyl)-4-(5-(4-methoxyphenyl) oxazol-2-yl) pyridinium bromide, and 3-(4-carboxybenzoyl) quinoline-2-carboxaldehyde, 3-(2-furoyl)quinoline-2-carboxaldehyde. In one embodiment, the proteins are labeled with a dye with minimum interference from background protein or retinol fluorescence. Such background interference may come from internal aromatic amino acid residues on RBP, or from retinol itself. Therefore, a dye that absorbs and emits at a wavelength distinct from RBP or retinol would be desirable in the teachings disclosed herein.

One embodiment provides the use of an ALEXA FLUOR® dye (fluorescent chemicals and biomolecule labeling kit, Molecular Probes, Inc.), with an absorbance spectra between 380 and 480 nm and an emission spectra between 520 and 600 nm. For example, ALEXA FLUOR® 430 absorbs at 430 nm, and emits at approximately 540 nm. One of ordinary skill in the art will appreciate the many varieties of dyes available to the practitioner to which, together with the disclosures presented herein, will allow a practitioner to select a fluorophore dye suitable for the purposes disclosed herein.

Proteins (such as TTR) may be labeled with fluorophores using commercially available kits, including ALEXA FLUOR®0 430 protein labeling kit (Molecular Probes, Inc., Eugene, Oreg.). Alternatively, proteins may be labeled wherein the fluorophore labels possess reactive linkers, see e.g. U.S. Pat. No. 6,140,041, herein incorporated by reference, or wherein the fluorophore labels covalently attach to the protein of interest. Other labeling means will become apparent to those of ordinary skill in the art dependent upon the type of fluorophore chosen.

The labels disclosed herein may also comprise an acceptor fluorescence moiety, preferably for use in fluorescence resonance energy transfer (FRET) detection. FRET detects signals representing a binding event, in which the fluorescence of a sample is altered by a change in the distance separating a fluorescence resonance energy donor moiety from a fluorescence resonance energy acceptor moiety that is either another fluorophore or a quencher. Combinations of a fluorophore and an interacting molecule or moiety are known as "FRET pairs." A transfer of energy between two members of a FRET-pair requires that the absorption spectrum of the second member of the pair overlaps the emission spectrum of the first member of the pair.

In FRET detection, the first probe comprises a first probe fluorescent donor or acceptor. The second probe comprises a second fluorescent donor or acceptor. The first fluorescent donor or acceptor and the second fluorescent donor or acceptor are selected to form a donor/acceptor pair comprising a fluorescent donor and a fluorescent acceptor capable of fluorescence resonance energy transfer with each other in response to activation of the fluorescent donor by light of a predetermined wavelength or band of wavelengths.

The excitation and emission spectra of a fluorescent moiety and the moiety to which it is paired determines whether it is a fluorescent donor or a fluorescent acceptor. The fluorescent dyes are selected so that the emission spectrum of the donor fluorophore overlaps the excitation spectrum of the acceptor fluorophore. Furthermore, in some methods, a donor fluorophore having a high extinction coefficient and low fluorescence quantum yield is paired with an acceptor fluorophore that does not strongly emit at the excitation wavelength of the donor fluorophore. A cyanine donor (e.g., CYA) and a rhodamine dye (e.g., R110, R6G, TAMRA and ROX) are an example of such a pair. Further guidance regarding the selection of donor and acceptor pairs that can effectively be used with the methods disclosed herein include: Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 1972³; and Haugland, Handbook of Fluorescent Probes and Research Chemicals, Molecular Probes, Eugene (1992).

The efficiency of fluorescence resonance energy transfer has been reported to be proportional to $D \times 10^{-6}$, where D is the distance between the donor and acceptor (Forster, Z. Naturforsch A, 4:321-327 (1949)). Accordingly, fluorescence resonance energy transfer typically occurs at distances of between 10-70 Å. Detection is performed by detecting light emitted by the fluorescent donor, the fluorescent acceptor, or both fluorescent donor and acceptor (i.e. a ratio). In one embodiment, the fluorescent donor and fluorescent acceptors are both fluorophores. The first fluorophore is activated with light of the appropriate wavelength or band of wavelengths, which is a function of the particular fluorophore. In an alternative embodiment, the fluorescent donor is a fluorophore and the fluorescent acceptor is a quencher and detection is performed by measuring the emission of the fluorophore.

In one embodiment, a member of the retinol-RBP-TTR complex is labeled with a fluorescent acceptor. For example, a fluorescent acceptor molecule may be attached to a TTR protein or polypeptide and subsequently detected through a FRET detection means. Representative flurophores that may be used include N-((2-(iodoacetoxy)ethyl)-N-methyl)amino-7-nitrobenz-2-oxa-1,3-diazole, 4-dihexadecylamino-7-nitrobenz-2-oxa-1,3-diazole, 6-(N-(7-nitrobenz-2-oxa-1,3-diazol-4-yl)amino)hexanoic acid, succinimidyl 6-(N-(7-nitrobenz-2-oxa-1,3-diazol-4-yl)amino)hexanoate, lucifer yellow iodoacetamide, N-(5-aminopentyl)-4-amino-3,6-disulfo-1,8-naphthalimide, N,N'-dimethyl-N-(iodoacetyl)-N'-(7-nitrobenz-2-oxa-1,3-diazol-4-yl)ethylenediamine, 1-(2-maleimidylethyl)-4-(5-(4-methoxyphenyl)oxazol-2-yl) pyridinium methanesulfonate, 1-(2,3-epoxypropyl)-4-(5-(4-methoxyphenyl)oxazol-2-yl)pyridinium trifluoromethanesulfonate, 1-(3-(succinimidyloxycarbonyl)benzyl)-4-(5-(4-methoxyphenyl)oxazol-2-yl) pyridinium bromide, and 3-(4-carboxybenzoyl)quinoline-2-carboxaldehyde, 3-(2-furoyl)quinoline-2-carboxaldehyde. The proteins may be labeled with an ALEXA FLUOR® dye, with an absorbance spectra between 380 and 480 nm and an emission spectra between 520 and 600 nm.

In one embodiment, a retinol-RBP-TTR protein complex, wherein TTR is labeled with an acceptor fluorophore, may be excited with light between 275 and 295 nm, and the emission wavelength measured at between 330 and 650 nm. Although not bound by any particular theory, it is believed that aromatic amino acid groups on RBP act as donor fluorophores and donate electrons to retinol, which acts as both an acceptor and donor fluorophore. The approximately 340 nm emission from the activated aromatic amino acid groups on RBP, therefore, excites retinol, which absorbs at approximately 325 nm, and in turn, emits at approximately 470 nm which excites the acceptor fluorophore groups on the labeled TTR, allowing FRET detection at an emission wavelength characteristic of the acceptor fluorophore. Aromatic amino acids absorb light at a wavelength of approximately 280 nm, and emit at approximately 325-350 nm, depending on the assay environment.

Figure 2:
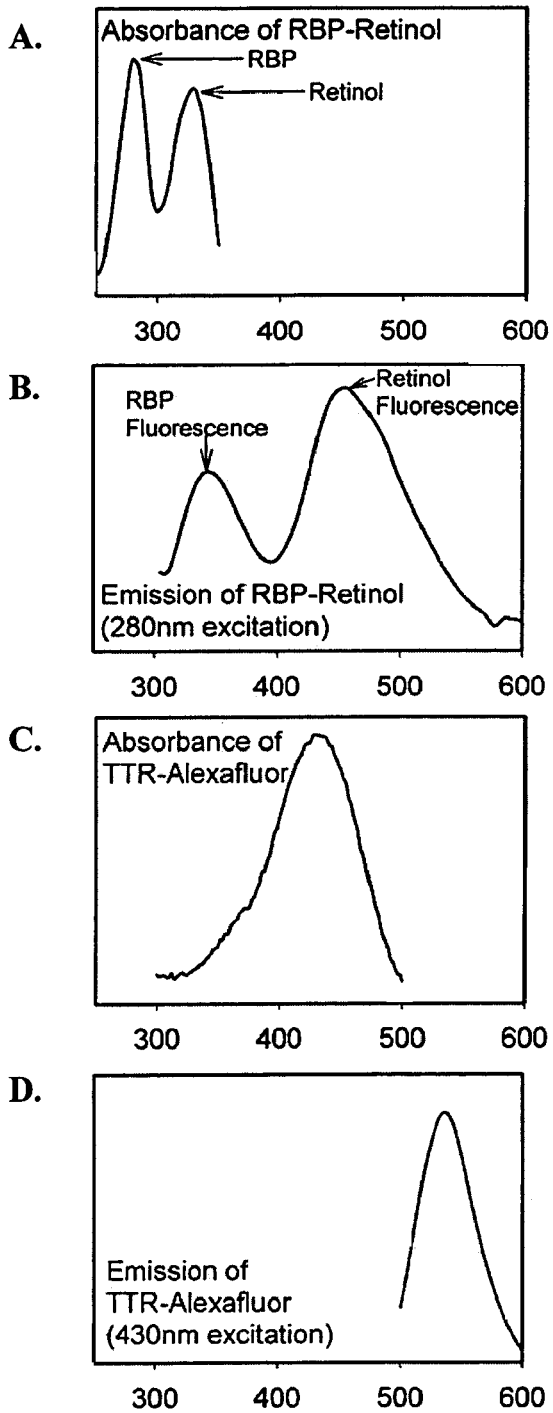
FIG. 2 illustrates FRET detection of TTR-RBP-retinol complex formation with labeled TTR.
Figure 2:
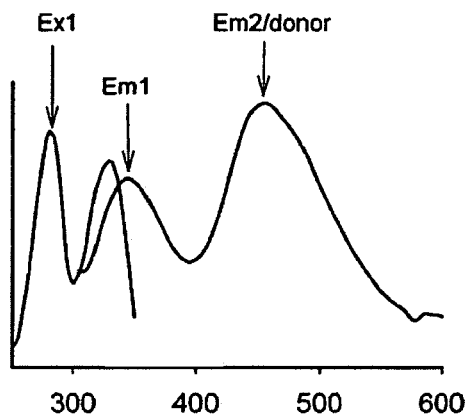
Figure 2:
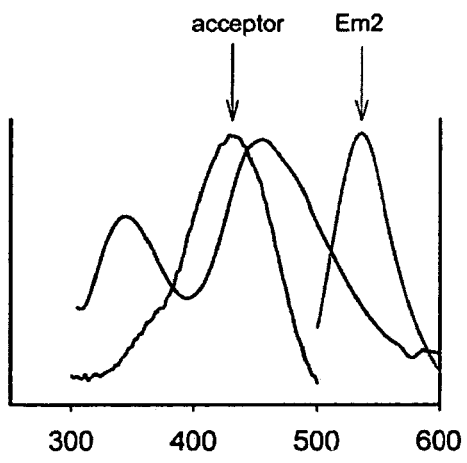

FIG. 2 is a depiction of FRET detection with labeled TTR. The absorbance and excitation emission spectra of RBP and retinol is shown in FIGS. 2A, 2B and 2E. Excitation of RBP, through excitation of aromatic amino acid residues, occurs at 280 nm and produces emission at 340 nm. Absorbance of TTR labeled with ALEXA FLUOR® 430 (FIGS. 2C-2E) occurs at 430 nm, with emission at 540 nm. Upon excitation of the labeled retinol-RBP-TTR complex at 280 nm, an emission radiation signal at approximately 540 nm wavelength will be detected through FRET to the acceptor ALEXA FLUOR® 430 label on TTR (see FIG. 2E).

In an alternative embodiment, a retinol-RBP-TTR protein complex, wherein TTR is labeled with an acceptor fluorophore, may be excited with light between 315 and 345 nm, and the emission wavelength measured at between 525 and 600 nm (see FIG. 2). Although not bound by any particular theory, it is believed that energy transfer from retinol to the acceptor fluorophore on a labeled TTR takes place, resulting in an emission wavelength characteristic of the acceptor fluorophore (see FIG. 2E).

Assay Conditions

An exemplary embodiment of the methods and compositions disclosed herein is to detect and/or quantitate retinol-RBP-TTR complex in a sample, which requires conditions conducive to retinol-RBP-TTR complex formation. One embodiment is to incubate RBP, TTR and retinol in physiological conditions, e.g. in phosphate buffered saline (PBS) or the equivalent. Alternatively, other conditions that approximate physiological conditions in vitro may also be used. Other embodiments include incubation in appropriate solvents, such as ethanol or hexane, see, e.g., Ong, D. E., J. Biol. Chem., 259:1476-1482 (1984), or other buffer formulations which allow retinol-RBP-TTR complex formation. In further embodiments, dimethylsulfoxide is added to the sample to promote the solubility of potential modulators of retinol-RBP-TTR complex formation. Amounts of dimethylsulfoxide up to at least 8% by volume may be added without adversely inhibiting (by itself) retinol-RBP-TTR complex formation. Further, the sample may be fresh or frozen until needed without adversely inhibiting (by itself) retinol-RBP-TTR complex formation.

Purified protein components, including TTR and RBP, may be used in conjunction with the teachings disclosed herein. Examples of purification of TTR and RBP are found in Berni et al., Anal. Biochem., 150:273-277 (1985); Peterson, P. A., J. Biol. Chem., 246:34-43 (1971); Berni and Lamberti, Comp. Biol. Chem., 94B:79-83 (1989); Ong, D. E., J. Biol. Chem., 259:1476-1482 (1984), herein incorporated by reference in its entirety. Purification includes any improvement in the amount of desired protein in a sample relative to the native sample (for example, if a native sample contains 1.5% of a desired protein, purification includes steps that increase the amount of desired protein in a sample derived from that native sample to more than 1.5%). Alternatively, the components of the methods and compositions disclosed herein may be naturally occurring in a biological sample from a mammal. For example, labeled TTR may be added to a biological sample from a mammal, and potential modulators tested according to the methods and compositions disclosed herein. The mammal is preferably a human, however other mammals, such as primates, horse, dog, sheep, goat, rabbit, mice or rats may also be used. A biological sample may comprise, but is not limited to, plasma, blood, urine, feces, tears or saliva.

Upon formation of the retinol-RBP-TTR complex, a potential modulator is added to the reaction mix and disruption of the complex monitored by monitoring label activity, for example fluorescence strength. A decrease in fluorescence as compared to a reaction mixture without added modulator, for example, will indicate disruption of the complex by the modulator. Conversely, no change in fluorescence activity will indicate non-disruption of the retinol-RBP-TTR complex. Addition of the potential modulator may occur before, during or after complex formation.

The compounds and compositions disclosed herein can also be used in assays utilizing a reagent comprised of a retinol-RBP-TTR complex formation member attached to a solid support. For example, RBP or labeled TTR may be attached to biotin, and subsequently bound to a solid support coated or modified with strept/avidin. Alternatively, RBP or labeled TTR may be derivatized and conjugated to active groups on the surface of the solid phase support. Examples of derivatizing protein or peptides for binding assays can be found in U.S. Pat. Nos. 4,478,946; 5,169,756, herein incorporated in its entirety by reference. Proteins or polypeptides may alternatively be adsorbed onto the solid phase. Coupling or adsorption of the protein or polypeptide may be followed by non-specific blocking of exposed binding sites on the surface of the solid phase.

The solid phase may be a test tube wall or microtiter plate, or may be a glass or silicon slide, microarray, microchip or other semi-conductor or microanalysis platform for attaching proteins or peptides to a solid phase. Alternatively, the solid phase may also be a bead (nanoparticle, microparticles, magnetic beads or the like) comprising agarose, polystyrene, latex, semi-conductor materials and polymethacrylate.

The assay can be performed either without separation (homogeneous) or with separation (heterogeneous) of any of the assay components or products. The present methods and compositions find particular use in homogeneous assays where the reactions can be carried out in solution phase. In these assays any dissociation of a labeled retinol, RBP, or TTR member into free label can reduce the sensitivity of the assay since binding of, for example, unlabeled TTR can compete with binding of labeled TTR that in turn is related to the presence or amount of modulator to be determined.

Heterogeneous assays usually involve one or more separation steps and can be competitive or non-competitive. A variety of competitive and non-competitive heterogeneous assay formats are disclosed in U.S. Pat. No. 5,089,390, incorporated herein by reference. In a typical competitive heterogeneous assay, a support having an antigen for analyte bound thereto is contacted with a medium containing the sample and analyte conjugated to a detectable label, such as an enzyme (the "conjugate"), fluorescent moiety or radiolabel. The analyte in the sample competes with the conjugate for binding to the antibody. After separating the support and the medium, the label activity of the support or the medium is determined by conventional techniques and is related to the amount of analyte in the sample.

A typical non-competitive sandwich assay is an assay disclosed in U.S. Pat. No. 4,486,530, incorporated herein by reference. In this method, a sandwich complex, for example an immune complex, is formed in an assay medium. The complex comprises the analyte, a first antibody, or binding member, that binds to the analyte and a second antibody, or binding member that binds to the analyte or a complex of the analyte and the first antibody, or binding member. Subsequently, the sandwich complex is detected and is related to the presence and/or amount of analyte in the sample. The sandwich complex is detected by virtue of the presence in the complex of a label wherein either or both the first antibody and the second antibody, or binding members, contain labels or substituents capable of combining with labels.

Sandwich assays find use for the most part in the detection of antigen and receptor analytes. In the assay, the analyte is bound by two receptor moieties, or antibodies, specific for the analyte. In one approach a first incubation of unlabeled antibody, or binding member, coupled to a support, otherwise known as the insolubilized binding group, is contacted with a medium containing a sample suspected of containing the analyte. After a wash and separation step, the support is contacted with a medium containing the second antibody or binding member, which generally contains a label, for a second incubation period. The support is again washed and separated from the medium and either the medium or the support is examined for the presence of label. The presence and amount of label is related to the presence or amount of the analyte. For a more detailed discussion of this approach see U.S. Pat. Nos. Re 29,169 and 4,474,878, the relevant disclosures of which are incorporated herein by reference.

In a variation of the above sandwich assay, the sample in a suitable medium is contacted with labeled antibody or binding member for the analyte and incubated for a period of time. Then, the medium is contacted with a support to which is bound a second antibody, or binding member, for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference.

In another variation of the above, the sample, the first antibody (or binding member) bound to a support and the labeled antibody (or labeled binding member) are combined in a medium and incubated in a single incubation step. Separation, wash steps and examination for label are as described above. For a more detailed discussion of this approach see U.S. Pat. No. 4,244,940, the relevant disclosure of which is incorporated herein by reference.

Homogenous assays require no separation of assay components, and is particularly useful in conjunction with high-throughput assays. Therefore, one embodiment is to provide a means for a homogeneous assay for detecting and/or quantitating modulators of TTR-RBP-retinol complex formation. In particular, the fluorescence resonance energy transfer assays are amenable to a homogeneous assay format. In fluorescence resonance energy transfer, a fluorescent signal is not detected unless an energy transfer event between a donor fluorescent moiety and an acceptor fluorescent moiety occurs. In the absence of a binding event, therefore, there is a minimal necessity for separating the labeled and unlabeled components. Similarly, there is a minimal necessity for separation of the labeled and unlabeled components if no perturbation of the complex after formation occurs when an agent is added to the mixture. Therefore, one other aspect is to provide a homogenous assay format utilizing FRET detection of a disruption of complex formation of TTR, RBP and retinol.

The methods and compositions disclosed herein also have application to all of the above heterogeneous assays, wherein the disruption of the binding event above is monitored following addition of the modulator. For example, the insolubilized binding member, either labeled TTR or RBP, can be formed by combining avidin bound to a support with a bis-biotin compound on the labeled TTR or RBP, in accordance with the teachings disclosed herein. This may be done prior to, during or after the formation of the labeled TTR-RBP-retinol complex. A potential modulator of TTR-RBP-retinol complex formation can then be added, and fluorescence monitored to determine if disruption has occurred. Alternatively, or in conjunction therewith, the labeled TTR or RBP can also be bound to the solid substrate, and subsequently the modulator is added together with the other components of the TTR-RBP-retinol complex.

In Vivo Detection of Modulator Activity

In addition to the in vitro methods disclosed above, the methods and compositions disclosed herein may also be used in conjunction with in vivo detection and/or quantitation of modulator activity of the TTR-RBP-retinol complex formation. For example, labeled TTR may be injected into a subject, wherein a candidate modulator was added before, during or after the injection of the labeled TTR. The subject may be a mammal, for example a human; however other mammals, such as primates, horse, dog, sheep, goat, rabbit, mice or rats may also be used. A biological sample is then removed from the subject and the label detected. A biological sample may comprise, but is not limited to, plasma, blood, urine, feces, mucus, tissue, tears or saliva.

Measurement of Label

The labeled reagents disclosed herein may take place using any of the conventional means known to those of ordinary skill in the art, depending upon the nature of the label. For example, a schematic of one example of a device that may be used with the fluorescence methods described herein is presented in FIG. 3; the various mirrors and lenses depicted within this figure are for illustrative purposes and not to provide a limitation to the design of the device that may be used with the detection, measurement and analytical methods described herein. The light is provided from a source (as described elsewhere herein) which is subsequently passed through a double-grating excitation spectrometer, which can comprise a series of mirrors and lenses. In addition the double-grating excitation spectrometer may include a microprocessor and associated software for controlling the action of the-mirrors and lenses, as well as for recording any information regarding the properties of the light passing through the double-grating excitation spectrometer. Other methods and designs for manipulating, controlling and/or measuring the light prior to contact with the sample may be used in such a device.

Figure 3:
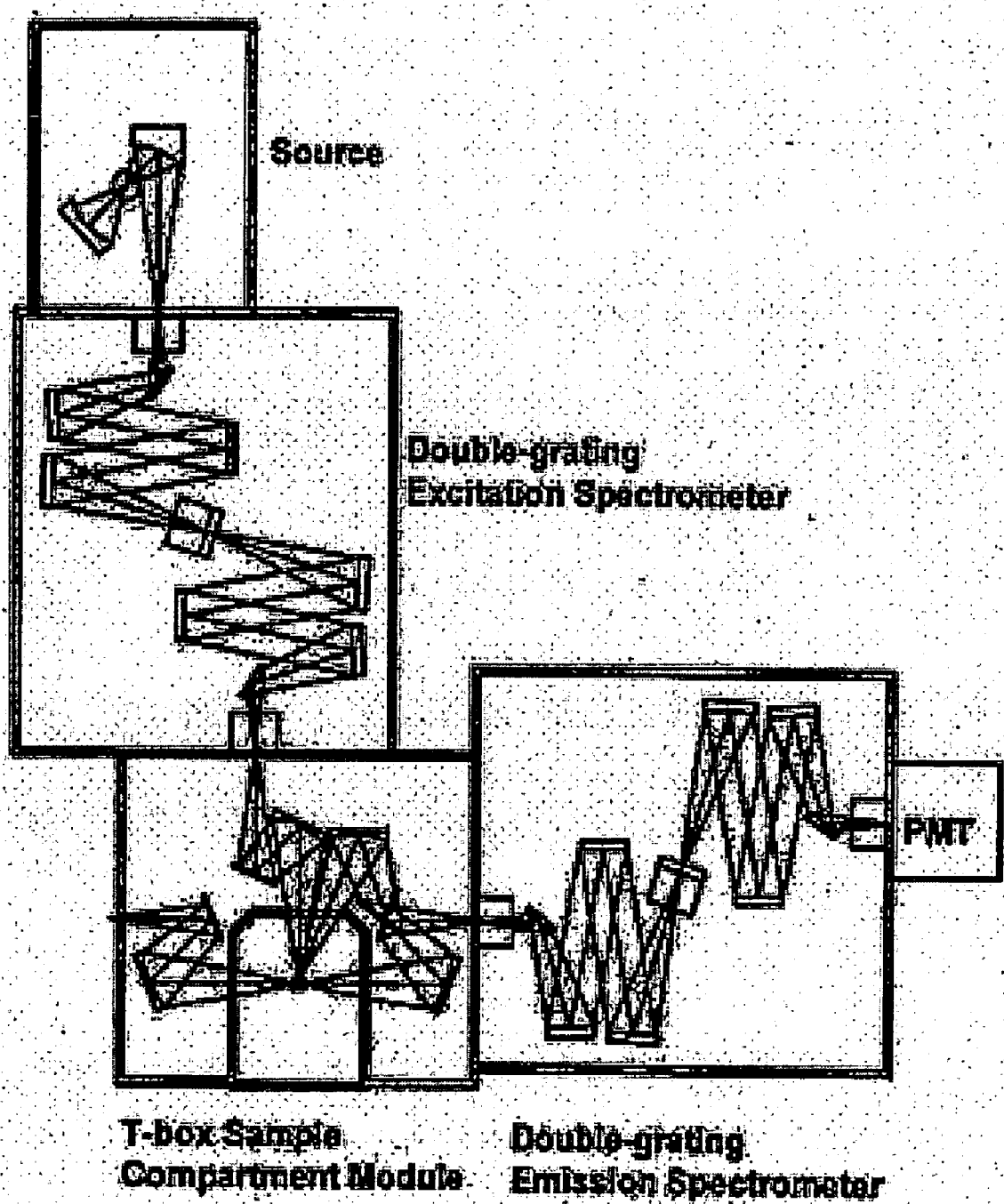
FIG. 3 presents a schematic of one example of the instrumentation for detecting and/or measuring the presence of fluorescent compounds in a sample.

After passing through the double-grating excitation spectrometer, the light passes through a sample compartment; in the case of FIG. 3, the sample compartment is designed as a T-box sample compartment module although other designs are considered well within the scope of the devices described herein. A series of lenses and mirrors may also be arranged within the sample module. In addition, the sample module may also reside within the double-grating spectrometers; i.e., the sample compartment does not have to exist as a distinct module. The components and properties of the sample compartment module may also be controlled, monitored and/or recorded using a microprocessor and associated software, or by means of an analog device, or more directly by the end-user of the device. After the source light interacts with the sample, the resultant light from the sample (via reflection, emission, transmission, and the like) can be further analyzed. A portion of the source light may also be used as a reference beam, in which case the reference beam may not make contact with the sample. In the example device presented schematically in FIG. 3, the resultant light (also described herein as the measured light and the received light) can further pass through a series of mirrors and lenses within the sample compartment; in addition, a portion of the resultant light may also be sent to other devices or instruments.

In FIG. 3, after passing through the series of optional mirrors and lenses in the sample compartment, the resultant light passes through a double-grating emission spectrometer, which may include a further series of lenses and mirrors. As with the double-grating excitation spectrometer, the double-grating emission spectrometer may include a microprocessor and associated software for controlling the action of the mirrors and lenses, as well as for recording any information regarding the properties of the light passing through the double-grating emission spectrometer. Other methods and designs for manipulating, controlling and/or measuring the light after contact with the sample may be used in such a device. In the final stage of the device presented schematically in FIG. 3, the resultant light interacts with a photomultiplier tube, which can be used as part of an instrument for recording the properties of the resultant light. Methods for recording, storing and analyzing the properties of the resultant light are described herein and may be incorporated into the device presented schematically in FIG. 3. Such a device may also include a means for providing a series of measurements, including but not limited to, various timing devices, choppers, and associated hardware, microprocessors, data storage devices, and software. In accordance with the teachings disclosed herein, measurements may take place only once; or multiple measurements, preferably at least two times, of the same sample may also be performed. If multiple measurements are taken, a brief delay in subsequent measurements may take place. In some embodiments, for example, at least ten seconds is given before subsequent measurements are taken. In other embodiments, non-specific background fluorescence is taken into account by separately measuring a sample, for example, of retinol-RBP-labeled TTR in the absence of potential modulators.

Devices suitable for the methods describe herein may include software for controlling the illumination step, the detecting step, archiving information, manipulating or deconvoluting images, data or information from the detection step, and the like.

Examples of monitoring devices for chemiluminescence, radiolabels and other labeling compounds can be found in U.S. Pats. No. 4,618,485; 5,981,202, the relevant disclosures of which are herein incorporated by reference.

High-Throughput Assays

The methods and compositions disclosed herein also relate to a high throughput assay for rapidly screening a plurality of modulators in conjunction with the methods and compositions disclosed herein. The assay detects and/or quantitates potential modulators of a retinol-RBP-labeled TTR complex, wherein the potential modulators or therapeutic candidates are added prior to, during or after complex formation. Inhibition of binding by the modulators or agents, which may include the library compounds disclosed above, causes a change in the amount of an optically detectable label that is attached to the TTR protein or polypeptide, the labeled TTR or RBP being optionally attached to solid supports. The degree of modulation is determined by measuring the amounts of label in solution, or in the case of an attached TTR or RBP, bound to the solid supports. These amounts are compared with the amount of label that is present in the absence of a modulator. Measurement may be performed using a high throughput optical device, including microtiter plate fluorescent readers or microchip array fluorescent readers. The assay may be homogeneous, i.e., no separation step is required to remove unbound label, since the amount of bound label is distinguished by scanning of the individual cells or solid supports. Alternatively, the assay may be heterogeneous with the inclusion of washing steps to remove any free components, e.g. uncomplexed labeled TTR. The method allows exceptional sensitivity and high throughput to be obtained in assays using small volumes, and small amounts of test compound.

Kits

One further embodiment is a kit for performing assays for screening for modulators using the methods and compositions disclosed herein. The kit comprises a TTR probe and a means for labeling the TTR protein or polypeptide. The TTR may be labeled with a fluorescent molecule, including a fluorescent acceptor moiety, in accordance with the embodiments disclosed herein. Alternatively, the kit may comprise RBP and retinol, and the TTR may be either free or attached (either bound or adsorbed) to a solid support.

Treatment Methods, Dosages and Combination Therapies.

There is a wide variety of treatments and therapies patients may consider for macular or retinal degenerations and dystrophies, which include: photodynamic therapy (PDT), low dose radiation therapy, submacular surgery, RPE transplantation, macular translocation surgery, laser treatment of drusen, and medications which can include an effective amount of a retinyl derivative, including derivatives of all-trans-retinal and 13-cis-retinal.

Other methods may be used to treat macular degenerations and dystrophies, retinal degenerations, and geographic atrophy. Thus, administration of a therapeutically effective amount of a compound of Formula (I) to a human having a macular degeneration (including both the wet forms and dry forms of age-related macular degeneration), macular dystrophy, retinal degeneration and/or geographic atrophy can be used to treat such conditions. Thus, fenretinide and its active metabolites may be so administered. For such treatment methods, doses, pharmaceutical formulations and additional experimental details see U.S. Provisional Pat. App. No. 60/582,293, filed Jun. 23, 2004 and U.S. Provisional Pat. App. No. 60/602,675, filed Aug. 18, 2004, U.S. Provisional Application Ser. No. 60/625,532 filed Nov. 4, 2004, U.S. Provisional Application Ser. No. 60/629,695, filed on Nov. 19, 2004, U.S. Provisional Application Ser. No. 60/660,904, filed on Mar. 11, 2005, and U.S. Provisional Application Ser. No. 60/672,405, filed on Apr. 18, 2005, the disclosures of which are specifically included in their entirety.

Further combinations that may be used to provide benefit to an individual include the use of genetic testing to determine whether that individual is a carrier of a mutant gene that is known to be correlated with certain ophthalmic conditions. By way of example only, defects in the human ABCA4 gene are thought to be associated with four distinct retinal phenotypes including Stargardt disease, cone-rod dystrophy, age-related macular degeneration and retinitis pigrnentosa. Such patients would be expected to find therapeutic and/or prophylactic benefit in the methods described herein.

In addition to the aforementioned ingredients, the formulations disclosed herein may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

EXAMPLES

The following ingredients, processes and procedures for practicing the methods disclosed herein correspond to that described above. The procedures below describe with particularity a presently preferred embodiment of the process for the detection and screening of modulators to retinol binding. Any methods, materials, reagents or excipients which are not particularly described will be generally known and available those skilled in the assay and screening arts.

Example 1

Labeling of TTR

TTR (Sigma Chemical Co.) was dissolved in phosphate buffered saline (PBS) buffer (pH 7.2), and the protein concentration adjusted to about 2-3 mg/ml. Prior to labeling, 10% (v/v) of 1M NaHCO3 (pH 8.3) was added to raise the sample pH.

A 4-times molar excess of ALEXA FLUOR® 430 (Molecular Probes) stock solution (in DMSO) was added to the protein solution. The mixture was incubated at room temperature on a Nutator in the dark. After 30 min, another aliquot of the fluorescence probe was added at approximately the same quantity as the first aliquot. The mixture was incubated for another 30 minutes.

ALEXA FLUOR® 430 labeled-TTR was separated from the free probe using Econo-Pac 10 DG desalting column (Bio-Rad). The protein fraction was concentrated and the residue amount of free probe further removed using Centricon YM-3 (Millipore) concentration devices.

The absorbance of the labeled protein solution at 280 and 434 nm was measured using a spectrofluorimeter. The protein concentration was calculated according to the following equation:

$$TTR(M) = \frac{[A_{280} - (A_{434} \times 0.28)] \times \text{dilution factor}}{77600}$$

where 0.28 is the correction factor to account for the probe absorbance at 280 nm, and 77,600 cm$^{-1}$M$^{-1}$ is the molar extinction coefficient of TTR.

(a) The degree of labeling was then calculated according to the following equation:

$$\text{moles probe per mole protein} = \frac{A_{434} \times \text{dilution factor}}{16000 \times \text{protein concentration }(M)}$$

where 16,000 cm$^{-1}$M$^{-1}$ is the molar extinction coefficient of Alexa Fluor 430 at 434 nm.

Example 2

Fluorescent Measurement of TTR and RBP Binding 3 ml of 1 µM TTR or Alexa Fluor 430-labeled TTR was prepared in PBS buffer and placed in a 3-ml fluorescent cuvette. The emission spectrum was measured between 290 nm to 650 nm with the excitation wavelength at 280 nm, and emission spectrum between 340 nm to 650 nm with the excitation wavelength at 330 nm, using a Jobin-Yvon Fluorolog 3 spectrofluorimeter. The band pass of the spectrofluorimeter was set at 1.5 nm.

Small aliquots of concentrated holo-RBP (retinol bound to RBP) stock solutions was then sequentially added to the TTR solution. The final concentrations of RBP were 0.33 µM, 0.67 µM, 1 µM, 1.33 µM, 1.67 µM and 2 µM, respectively. After each addition, the sample was mixed and incubated at room temperature for 20 min. The fluorescence spectra was measured as above. The contribution of RBP to the emission was subtracted from the measured spectra by using blanks of RBP at appropriate concentrations.

Figure 4:
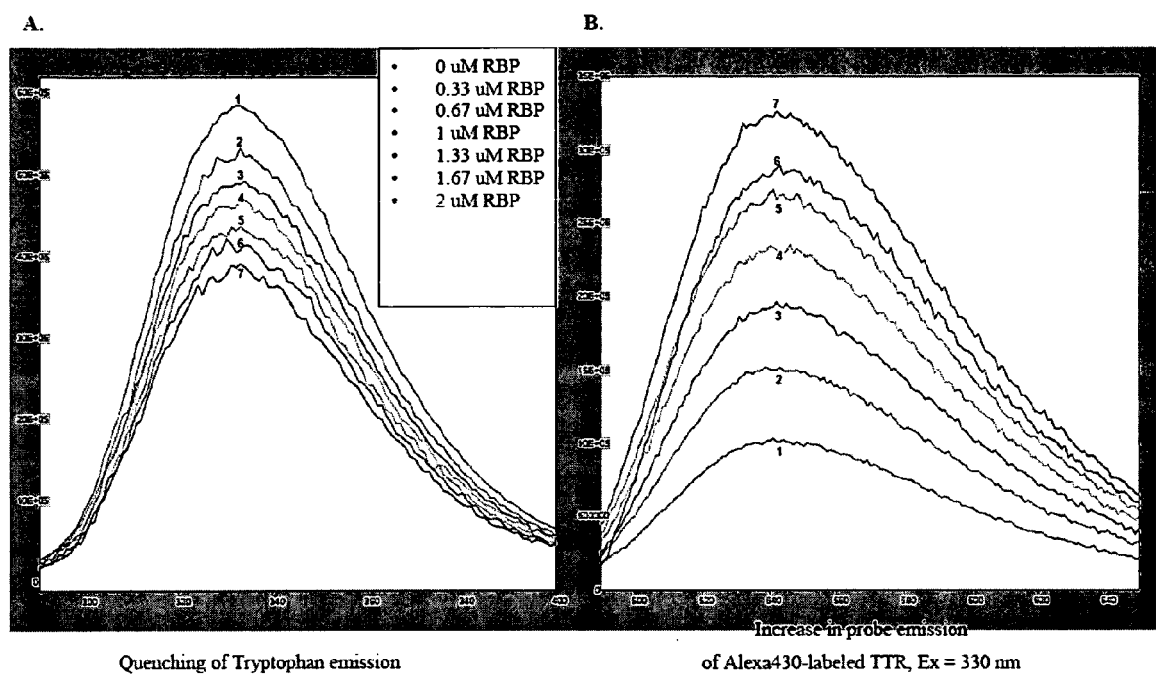
FIG. 4 illustrates results from aromatic amino acid quenching versus FRET detection of retinol-RBP-TTR complex formation.

Two emission peaks were particularly monitored, TTR protein emission at 330 nm (excitation at 280 nm), and Alexa Fluor 430 emission at 540 nm (excitation at 330 nm), at different RBP to TTR ratios (see FIG. 4).

Example 3

Comparison of Aromatic Amino Acid Quenching

The currently used method for detection of RBP-TTR interaction relies on quenching of TTR protein (aromatic amino acid) fluorescence in the present of increasing concentrations of RBP. Analysis of crude sera is not permissible in this assay due to the presence of other interfering proteins in sera. Therefore, RBP must be purified from crude sera prior to analysis of TTR binding. This is a time consuming process which is not amenable to high-throughput screening. An example of data obtained using this technique is provided in FIG. 4A. In FIG. 4A, the fluorescent emission of the retinol-RBP-unlabeled TTR complex is measured with excitation at 280 nm. The different curves in the graph represent increasing concentration of RBP added to the sample mixture. At higher amounts of RBP, where increasing levels of RBP are complexed to unlabeled TTR, the complexed RBP gradually quenches the aromatic amino acid fluorescent signal on TTR.

Figure 5:
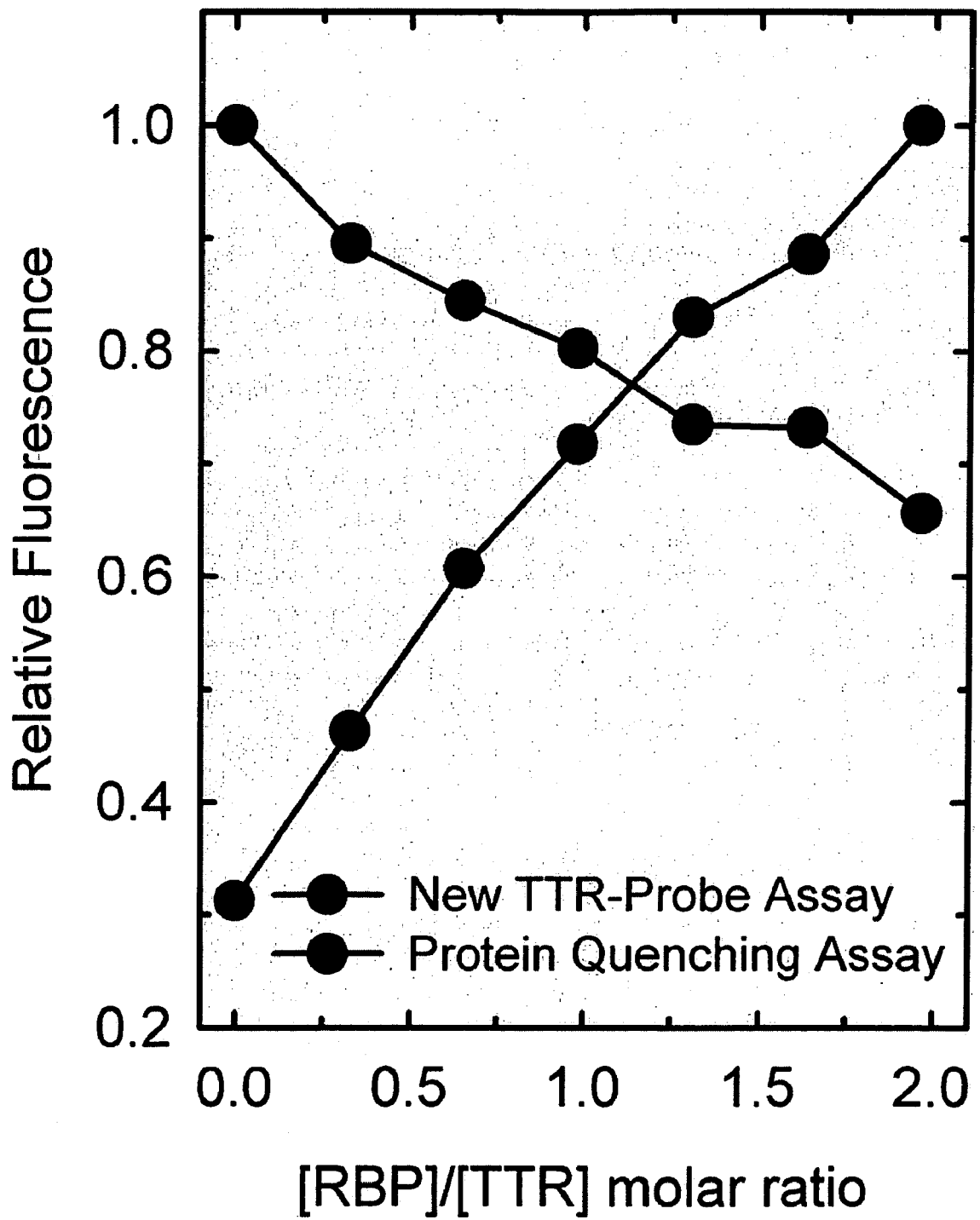
FIG. 5 illustrates results from aromatic amino acid quenching versus FRET detection of retinol-RBP-TTR complex formation.

In order to overcome limitations of the routine binding assay, a high-throughput assay was developed to examine the kinetics of RBP-TTR interaction (see FIG. 4B). In this assay, commercially prepared TTR is modified with a fluorescent probe which is excited only when a retinoid protein complex is bound to it (i.e. retinol-RBP). Thus, non-specific protein and/or unbound retinoid-protein species present in crude sera will not interfere with the detection of the RBP-labeled TTR complex. In addition, the assay is 2 to 3 times more sensitive and demonstrates a greater dynamic range and linearity for detection and quantitation. A direct comparison of the two techniques is provided (FIG. 5). The assay technique may be adapted to a 96-well plate format to facilitate screening of large numbers of samples in a high-throughput format.

Example 4

Figure 6:
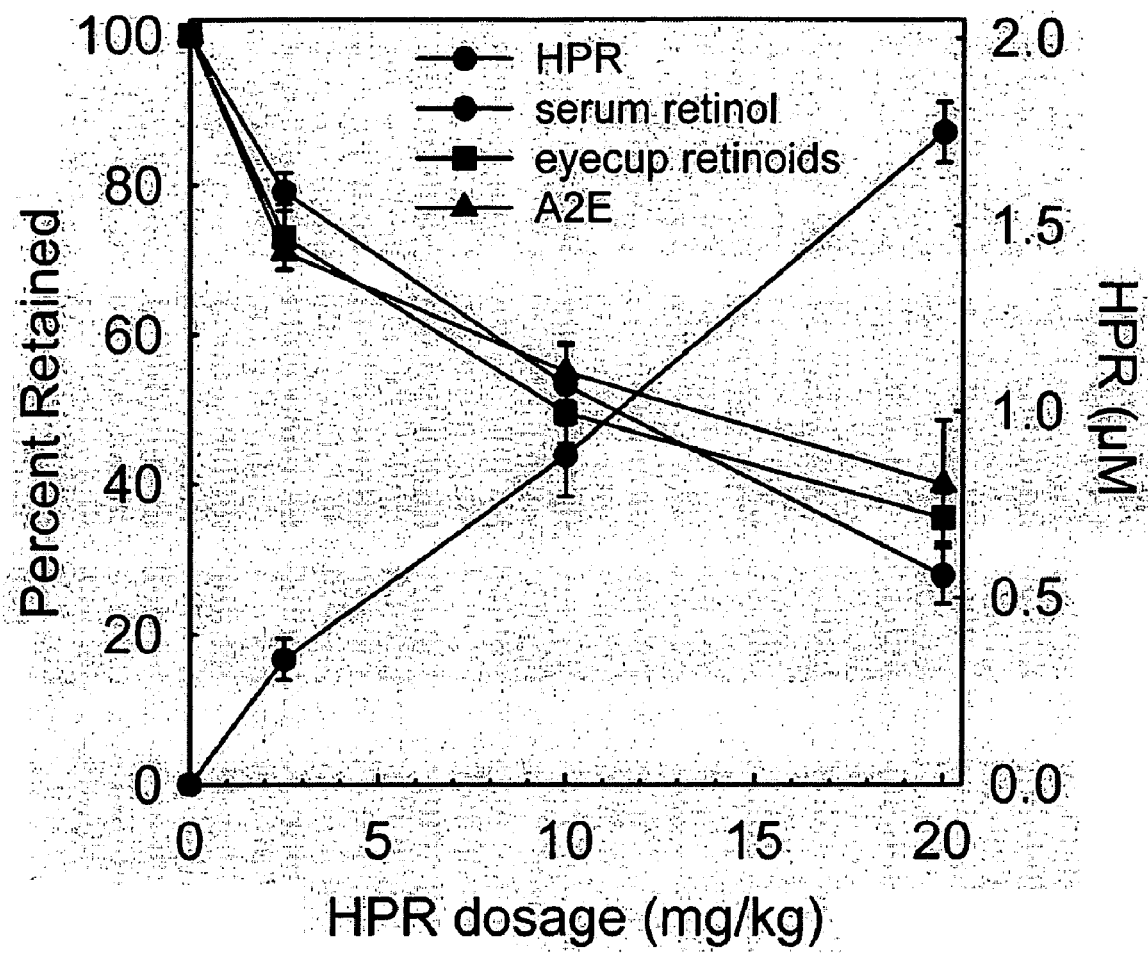
FIG. 6 illustrates the relationship of serum HPR levels to serum retinol levels and ocular levels of retinoids and A2E.

In-Vivo Analyses of the Relationship of Serum HPR Levels to the Levels of Serum Retinol, and Ocular Retinoids and A2E In in vitro assays, inhibition of LRAT activity results in a net reduction in the all-trans retinyl ester pool and, therefore, a reduction in 11-cis retinol. In order to further explore the role of HPR in the visual cycle, the in vivo effects of HPR in mice have been examined. Thus, HPR was administered to ABCA4 null mutant mice (5-20 mg/kg, i.p. in DMSO) for periods of 28 days. Control mice received only the DMSO vehicle. At the end of the treatment period, the concentrations of retinol and HPR in serum and retinoid content in ocular tissues was measured. Profound reductions in serum retinol as a function of increasing serum HPR was observed. This effect was associated with commensurate reductions in ocular retinoids and A2E (a toxic retinoid-based fluorophore). Thus, the calculated percent reduction for each of the measured retinoids, and A2E, was nearly identical (see FIG. 6). These results indicate that HPR has a limited effect on visual cycle proteins (e.g., LRAT) when administered systemically; instead these results indicate that reduction of ocular retinoides and A2E resulting from systemic administration of HPR results from reductions in serum retinol levels. If systemically-administered HPR inhibits ocular LRAT, then reduction of ocular retinoids and A2E should exceed the reduction in serum retinol.

Figure 7:
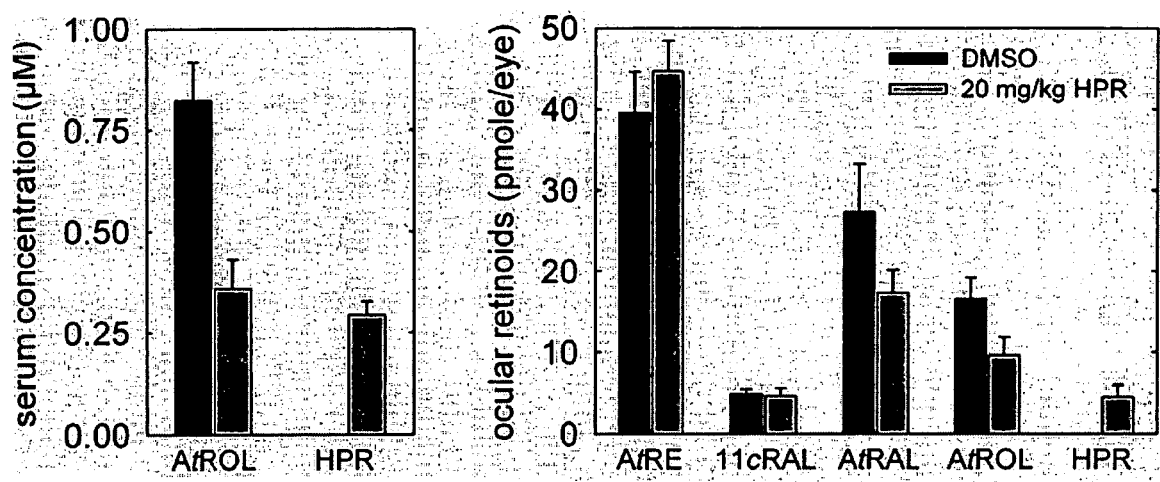
FIG. 7 illustrates the effect of administering HPR to wild type mice on (A) serum retinol levels and (B) ocular retinoid levels.

In order to ensure that the observed effects of HPR in ABCA4 null mice were not due to the genetic mutation, HPR (20 mg/kg, i.p. in DMSO) was administered to wild type mice for 5 days. Control mice received only the DMSO vehicle. On the final day of HPR treatment, the mice were exposed to constant illumination (1000 lux for 10 min) order "stimulate" the visual cycle to generate visual chromophore. Immediately following the illumination period, the animals were sacrificed and the concentrations of retinoids in serum and ocular tissue were determined. The data (see FIG. 7) reveal no significant inhibition in synthesis of either retinyl esters or visual chromophore. As in the previous study, HPR caused a significant reduction in serum retinol (~55%), ocular retinol (~40%) and ocular retinal (~30%). Although HPR did accumulate within ocular tissues during the treatment period (~5 µM), no effect on LRAT or Rpe65/isomerase activities was observed.

Genetic crosses of RBP4$^{-/-}$ mice with ABCA4$^{-/-}$ mice was undertaken to examine the role of RBP in mediation of retinol levels in serum and ocular tissue. Mice from the first generation of this cross (i.e., RBP4/ABCA4$^{+/-}$) show comparable levels of RBP-retinol reduction as observed in the HPR study when the administered dose was 10 mg/kg (~50-60% reduction in serum RBP-retinol). Moreover, the RBP4/ABCA4$^{+/-}$ mice show commensurate reductions in ocular retinol (~60% reduction). These findings are consistent with data obtained during pharmacological modulation of RBP-retinol with HPR and, therefore, strongly suggest that A2E-based fluorophores will be reduced proportionately.

The inhibition of LRAT activity observed during in vitro analyses has not been observed in mice receiving acute and chronic doses of HPR. Such differences in in vivo and in vitro observations may arise from the differential accessibility of HPR to visual cycle enzymes in vitro versus in vivo. That is, in the in vitro assays, HPR is pre-incubated with enzyme source material before the addition of substrate and initiation of the assay. HPR may become more accessible to visual cycle proteins during the pre-incubation and assay period and produce the observed results. The situation in vivo may be very different. As all of the enzymatic proteins of the visual cycle are hydrophobic in nature, accessibility by small polar molecules such as HPR may be significantly hindered.

Example 6

High-Throughput Assay for Detection of RBP/TTR Interaction

Figure 8:
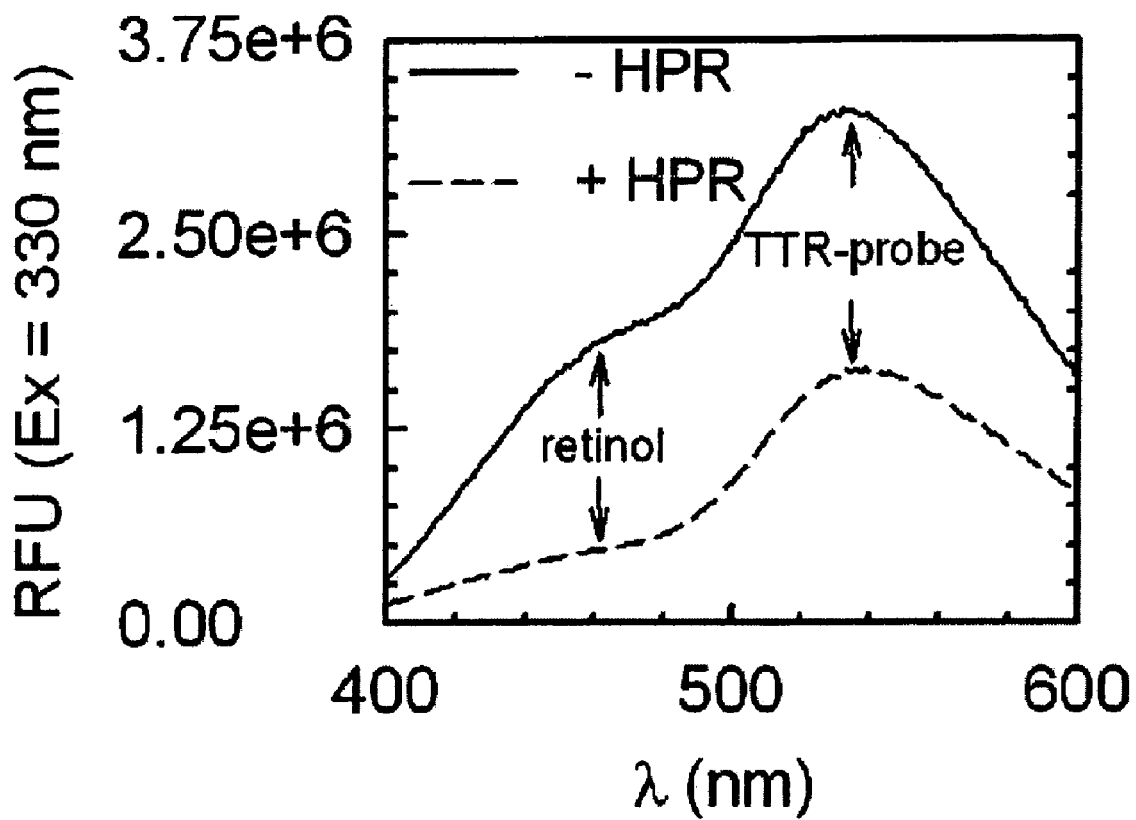
FIG. 8 illustrates an example of a FRET spectrum taken of an RBP-TTR complex in the absence and presence of HPR, wherein the TTR has been labeled with a fluorescence moiety.

Reduction of serum retinol and RBP are correlated with concomitant reductions in toxic lipofliscin fluorophores. Because compounds that affect RBP-TTR interaction will directly affect fluorophore levels in the eye, a high-throughput screen for small molecules which prevent interaction of RBP with TTR was developed. This screen employs probe-labeled forms of RBP and TTR which participate in a unique fluorescence resonance energy transfer (FRET) event when complexed. Compounds which interfere with RBP-TTR interaction prevent FRET. Sample spectra taken during the course of this type of assay are shown in FIG. 8. These data show interaction of RBP-TTR (0.5 µM unlabeled RBP+0.5 µM Alexa430-TTR) in the absence (solid line) and presence (dashed line) of HPR (1 µM). The sample is incubated at 37° C. for 30 min and then illuminated with 330 nm light. The emission spectra are shown in the range of 400-600 nm. HPR binds to RBP and prevents interaction with TTR, and here this property of HPR is utilized here to validate the ability of this screen to detect inhibition of RBP-TTR interaction. The presence of HPR is associated with significantly reduced retinol and TTR-probe fluorescence indicating loss of complexation. Additionally, the design of this assay permits discrimination between compounds which interact with RBP versus those which interact with TTR. Thus, by using two distinct excitation energies (280 nm and 330 nm, for protein and retinol, respectively) and implementing simultaneous monitoring of the retinol and TTR-probe fluorescence, the "target" of a presumptive small molecule can be easily determined.

Example 7

Adaptation and Optimization of Assay to 384-Well Plate Format

In order to facilitate screening of large numbers of test compounds, the RBP-TTR assay has been adapted to a 384-well plate format. This transition required re-evaluation of the reagent concentrations and minimal assay volume for maintaining solubility and detection sensitivity. Under the 384-well plate format, the assay can be efficiently performed in a 50 µl volume using 0.5 µM apo-RBP, 0.5 µM TTR, 2-8 µM test compound and 1 µM retinol. The microplate with minimal fluorescence background, best optical clarity and most appropriate well design was determined to be Corning's model #3711.

Dimethyl sulfoxide (DMSO) will be used to deliver test compounds to the RBP-TTR assay mixture. Further, in order to determine the kinetic properties of inhibition observed with a particular compound, the test compounds are evaluated at varied concentrations. The most convenient method of achieving this objective in a high-throughput assay is to add increasing volumes of a fixed compound concentration. This approach results in increasing concentrations of DMSO in the assay mixture. Accordingly, studies were carried out to determine the tolerance of the RBP-TTR assay for increasing concentrations of DMSO. It was determined that concentrations up to 8% DMSO, v/v had no effect on RBP-TTR interaction either in the absence or presence of HPR, which was used as the positive control for RBP-TTR inhibition.

An important consideration for generation of the TTR-AlexaFluor 430 protein is the molar amount of AlexaFluor 430 required to effectively label (and in certain circumstances, to optimally label) the TTR protein without compromising the inherent affinity of TTR for RBP. This concern has economical implications as the requirement for increased mol % of AlexaFluor 430 means increased cost. Studies were conducted to determine the lowest mole % of AlexaFluor 430 required to effectively label TTR without affecting binding to RBP. It was determined that 1.7 mol % of AlexaFluor 430 is required to label 1 mole of tetrameric TTR.

In order to further facilitate high throughput of the RBP-TTR assay, the test compounds will be added to master plates at one time and the plates stored at −20° C. for up to 2 weeks before adding retinol and conducting the assay. The present assay is quite stable under these conditions. No loss in sensitivity is observed after 2 weeks of storage at −20° C.

Example 8

Assay Validation and Comparison to Conventional Techniques

Figure 9:
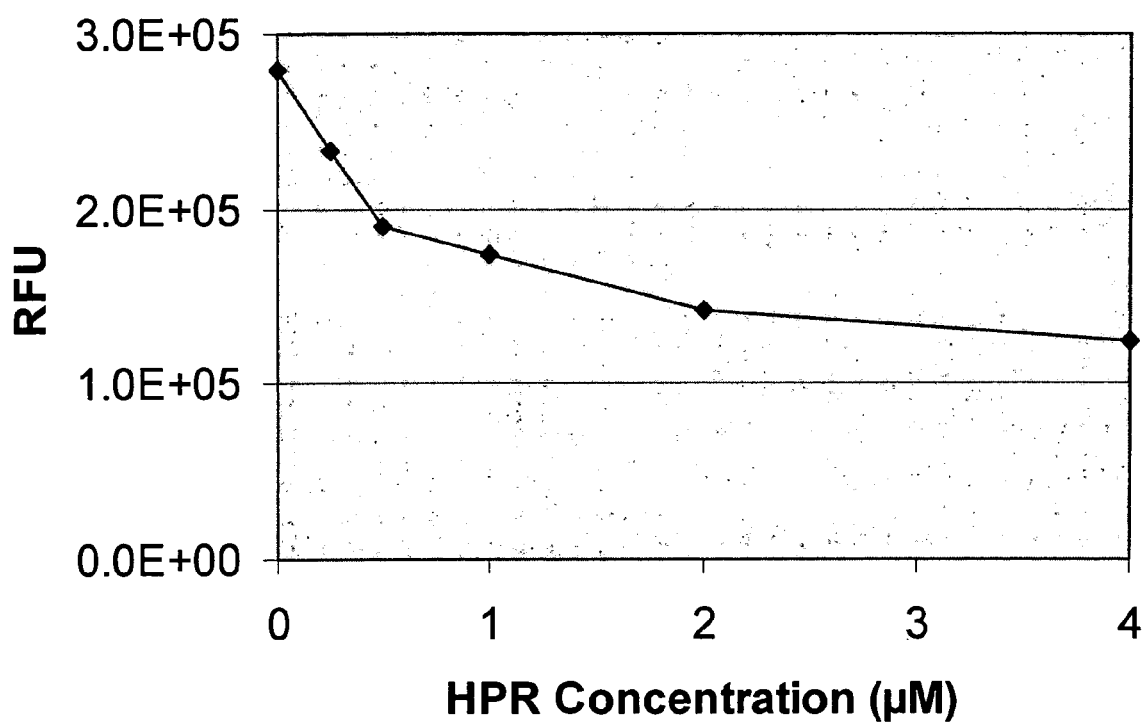
FIG. 9 illustrates an example of dose dependent inhibition of retinol-RBP-TTR complex formation by HPR as determined using the FRET methods described herein.

HPR is an effective inhibitor of RBP-TTR interaction as shown by chromatographic and spectrophotometric measurement techniques (See, e.g., Radu R A, Han Y, Bui T V, Nusinowitz S, Bok D, Lichter J, Widder K, Travis G H and Mata N L; Reductions in Serum Vitamin A Arrest Accumulation of Toxic Retinal Fluorophores: A Potential Therapy for Treatment of Lipofuscin-based Retinal Diseases, *Invest Ophthalmol. Vis Sci.*, in press (2005)). Thus, HPR may be used as a positive control to validate the capacity of the high throughput assay to detect inhibitors of RBP-TTR interaction. Accordingly, HPR was employed at varied concentrations (from 0-4 µM), using the conditions specified in Example 7, to evaluate the high throughput assay. As shown in FIG. 9, the high throughput assay is effective to detect compounds which, like HPR, inhibit RBP-TTR interaction.

Physiologically, RBP-retinol must complex with TTR in order to achieve a high steady-state concentration of RBP-retinol. This interaction creates a large molecular size complex which resists glomerular filtration and permits delivery of retinol to extra-hepatic target tissues. Inhibition of RBP-TTR interaction results in a reduction of circulating RBP as the relatively small sized RBP-ligand complex would be lost through glomerular filtration. The reduction in circulating RBP then causes a reduction in circulating retinol. This effect has been established in vivo for HPR by several investigators. This effect has also been observed in vivo using all-trans and 13-cis retinoic acids (See, e.g., Berni R, Clerici M, Malpeli G, Cleris L, Formelli F; Retinoids: in vitro interaction with retinol-binding protein and influence on plasma retinol, *FASEB J*. (1993) 7:1179-84).

Figure 10:
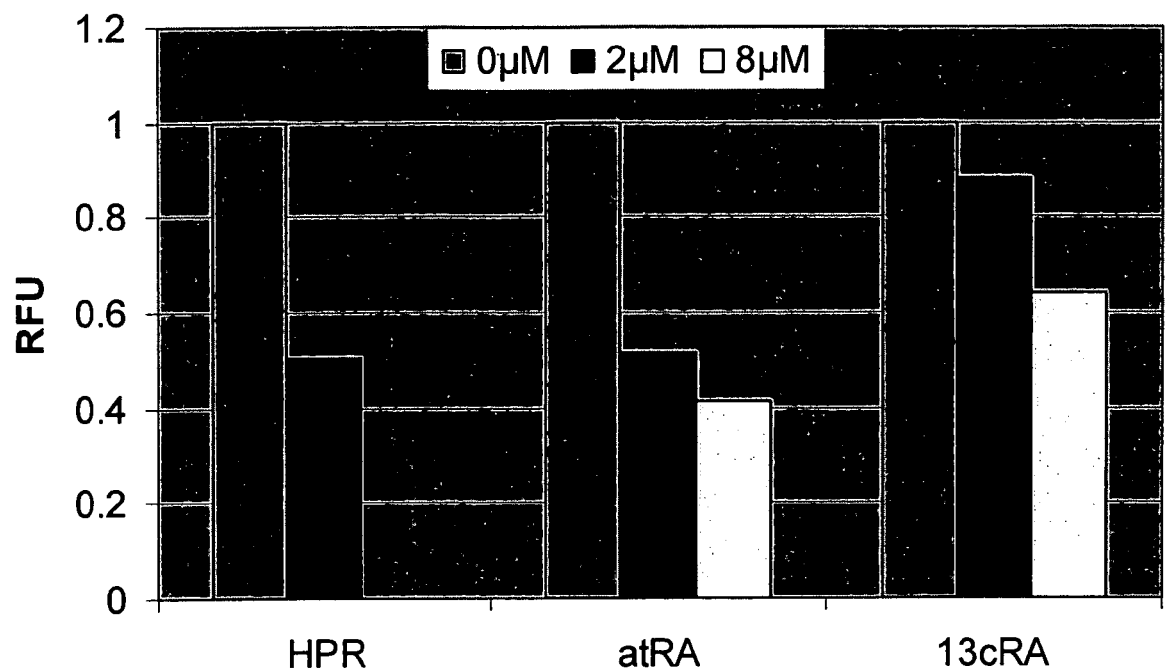
FIG. 10 illustrates a comparison of the inhibition of retinol-RBP-TTR complex formation using HPR, 13-cis-retinoic acid and all-trans-retinoic acid as determined using the FRET methods described herein.

The mechanism of action underlying this effect can be explained by the disruption of RBP-TTR interactions. In order to explore this possibility and to further validate the RBP-TTR screen, the effects of all-trans retinoic and 13-cis retinoic acid, using the conditions the conditions specified for analysis of HPR, were examined. The data obtained (see FIG. 10) are entirely consistent with the in vivo data. This finding further validates the ability of this assay to detect known physiological inhibitors of RBP-TTR interaction.

Example 9

Comparison of Assay to Conventional Techniques

Figure 11:
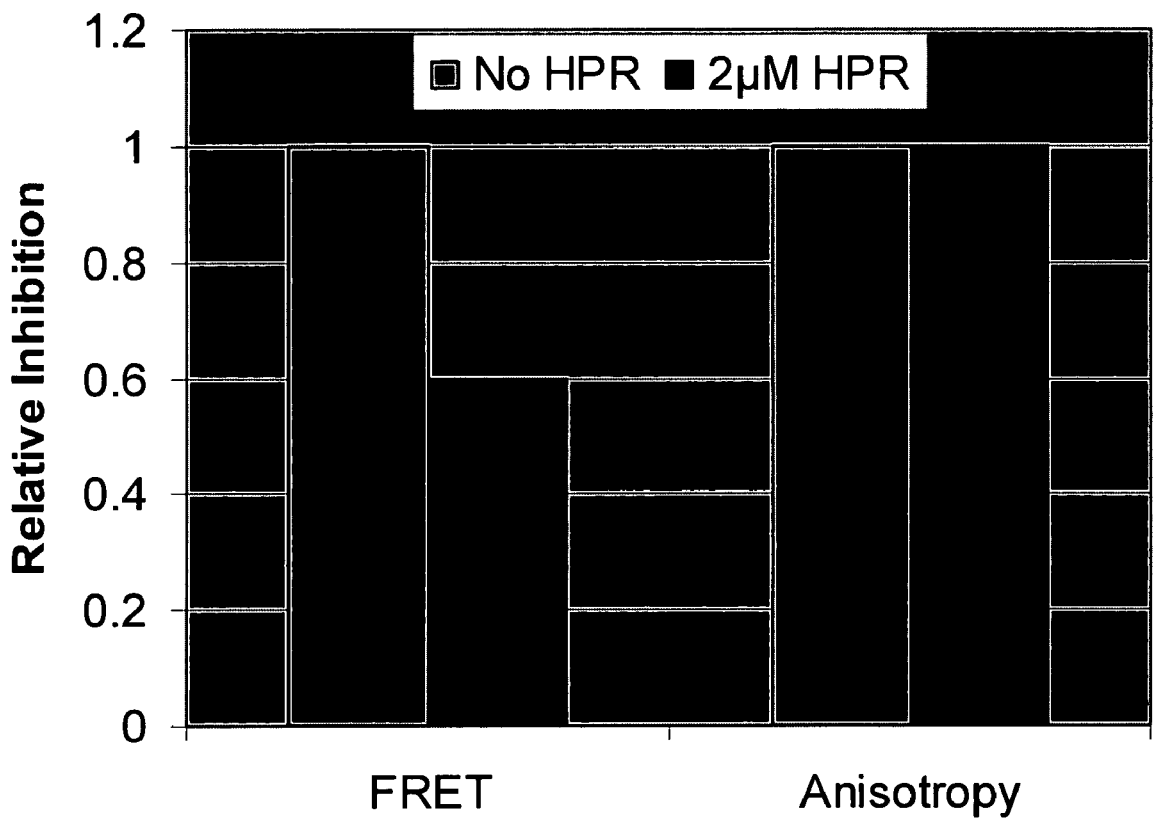
FIG. 11 illustrates a comparison of the inhibition of retinol-RBP-TTR complex formation using HPR as determined using the FRET methods described herein and fluorescence anisotropy methods.

Current high throughput methodologies used to detect complexation between two proteins are limited to those employing fluorescence techniques. A popular method is fluorescence anisotropy. This method, which measures change in molecular volume (or size), has been used successfully in analytical studies to measure interaction between RBP-retinol and TTR (see, e.g., van Jaarsveld PP, et al., *J Biol Chem.*, 248:4698-705 (1973); Kopelman M, et al., *Biochim Biophys Acta*. 439:449-60 (1976); Malpeli G, et al., *Biochim Biophys Acta.,* 1294:48-54 (1996)). In this approach, the fluorescence emission of retinol is monitored, at 0 and 90 degree angles, in the absence and presence of TTR. Although this technique is quite sensitive, it is not quantitative. Thus, the output value would be the same for all degrees of RBP-TTR binding. A binding of 100% of the RBP-retinol present in the assay to TTR could not be distinguished from a binding of only 10%. This shortcoming of the anisotropy technique is in FIG. 11. Here, the effect of HPR on RBP-TTR interaction is measured using our routine FRET (high-throughput) assay and by traditional fluorescence anisotropy.

In addition to the technical impasses of fluorescence anisotropy to screen for compounds which affect RBP-TTR interaction, few commercially available instruments are available with high throughput capability which offer fluorescence anisotropy with detection in the near UV range. On the other hand, the FRET assay which can be employed on any conventional fluorescent microplate reader.

All of the methods disclosed and claimed herein can be made and executed without undue experimentation in light of the present disclosure. It will be apparent to those of skill in the art that variations may be applied without departing from the concept, spirit and scope of the invention. More specifically, it will be apparent that certain agents that both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for treating dry forms of age related macular degeneration in a human in need comprising systemic administration of a therapeutically effective amount of a compound having the structure of Formula (I):

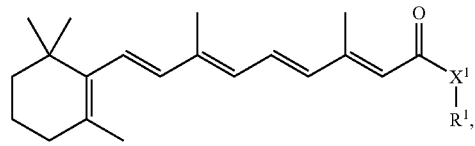

wherein $X^1$ is $NR^2$; $R^1$ is $(CHR^2)_x$-$L^1$-$R^3$, wherein x is 0; $L^1$ is a single bond; each $R^2$ is H; and $R^3$ is a mono-substituted aryl wherein said mono substituted aryl is 4-hydroxyphenyl or 4-methoxyphenyl.

2. The method of claim 1, wherein the macular degeneration is geographic atrophy.

3. The method of claim 1, wherein the macular degeneration is a macular dystrophy.

* * * * *